(12) United States Patent
Lombardo et al.

(10) Patent No.: US 6,740,092 B2
(45) Date of Patent: May 25, 2004

(54) METHODS AND TOOLS FOR FEMORAL INTERMEDULLARY REVISION SURGERY

(75) Inventors: Alan Lombardo, Elmwood Park, NJ (US); Stuart L. Axelson, Jr., Succasunna, NJ (US); James V. Bono, Dover, MA (US); Kenneth Krackow, Williamsville, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 342 days.

(21) Appl. No.: 09/758,608

(22) Filed: Jan. 11, 2001

(65) Prior Publication Data

US 2001/0001121 A1 May 10, 2001

Related U.S. Application Data

(62) Division of application No. 09/049,705, filed on Mar. 28, 1998.

(51) Int. Cl.[7] .......................... A61B 17/58; A61F 11/00; A61F 2/38
(52) U.S. Cl. ...................... 606/88; 606/108; 623/20.14
(58) Field of Search ........................... 606/86–88, 102; 623/20.14, 20.15

(56) References Cited

U.S. PATENT DOCUMENTS

| | | | | |
|---|---|---|---|---|
| 4,722,330 A | * | 2/1988 | Russell et al. | 606/88 |
| 4,926,847 A | * | 5/1990 | Luckman | 606/88 |
| 5,002,547 A | * | 3/1991 | Poggie et al. | 606/88 |
| 5,037,423 A | | 8/1991 | Kenna | 606/88 |
| 5,129,909 A | | 7/1992 | Sutherland | 606/88 |
| 5,364,401 A | * | 11/1994 | Ferrante et al. | 606/87 |
| 5,415,663 A | | 5/1995 | Luckman et al. | 606/86 |
| 5,683,397 A | * | 11/1997 | Vendrely et al. | 606/88 |
| 5,709,689 A | | 1/1998 | Ferrante et al. | 606/86 |
| 5,716,361 A | * | 2/1998 | Masini | 606/86 |
| 5,769,854 A | * | 6/1998 | Bastian et al. | 606/88 |
| 5,885,296 A | * | 3/1999 | Masini | 606/86 |
| 5,916,220 A | * | 6/1999 | Masini | 606/87 |
| 6,056,756 A | * | 5/2000 | Eng et al. | 606/87 |
| 6,077,270 A | * | 6/2000 | Katz | 606/88 |
| 6,120,509 A | * | 9/2000 | Wheeler | 606/87 |
| 6,193,723 B1 | * | 2/2001 | Cripe et al. | 606/88 |

FOREIGN PATENT DOCUMENTS

EP  0 555 003 A1  8/1993

* cited by examiner

*Primary Examiner*—Michael J. Milano
*Assistant Examiner*—Paul Roberts
(74) *Attorney, Agent, or Firm*—Lerner, David, Littenberg, Krumholz & Mentlik, LLP

(57) ABSTRACT

IM revision tools include reamers with depth markings or stops, an impactor-extractor with a coupling for attaching to tools which are inserted into and removed from the IM canal, a resection guide tower to which a cutting block is attached and which includes a notch which serves as both a witness mark and a holder for a femoral collar, a reversible clean-up cutting block with a quick-connect clamp attachable to the guide tower for resecting the distal femur, a selection of spacer blocks for measuring the space between the femur to determine the size of the components to be installed, a multiple cut cutting guide for preparing the femur, a set of 5 and 10 mm trial wedges, a trial stem valgus adapter, femoral sizing indicators which include indications of anterior/posterior offset, a stabilizer box cutting template which is attachable to the multiple cut cutting guide, and anterior/posterior offset adapters for attaching the femoral component to the IM stem.

20 Claims, 26 Drawing Sheets

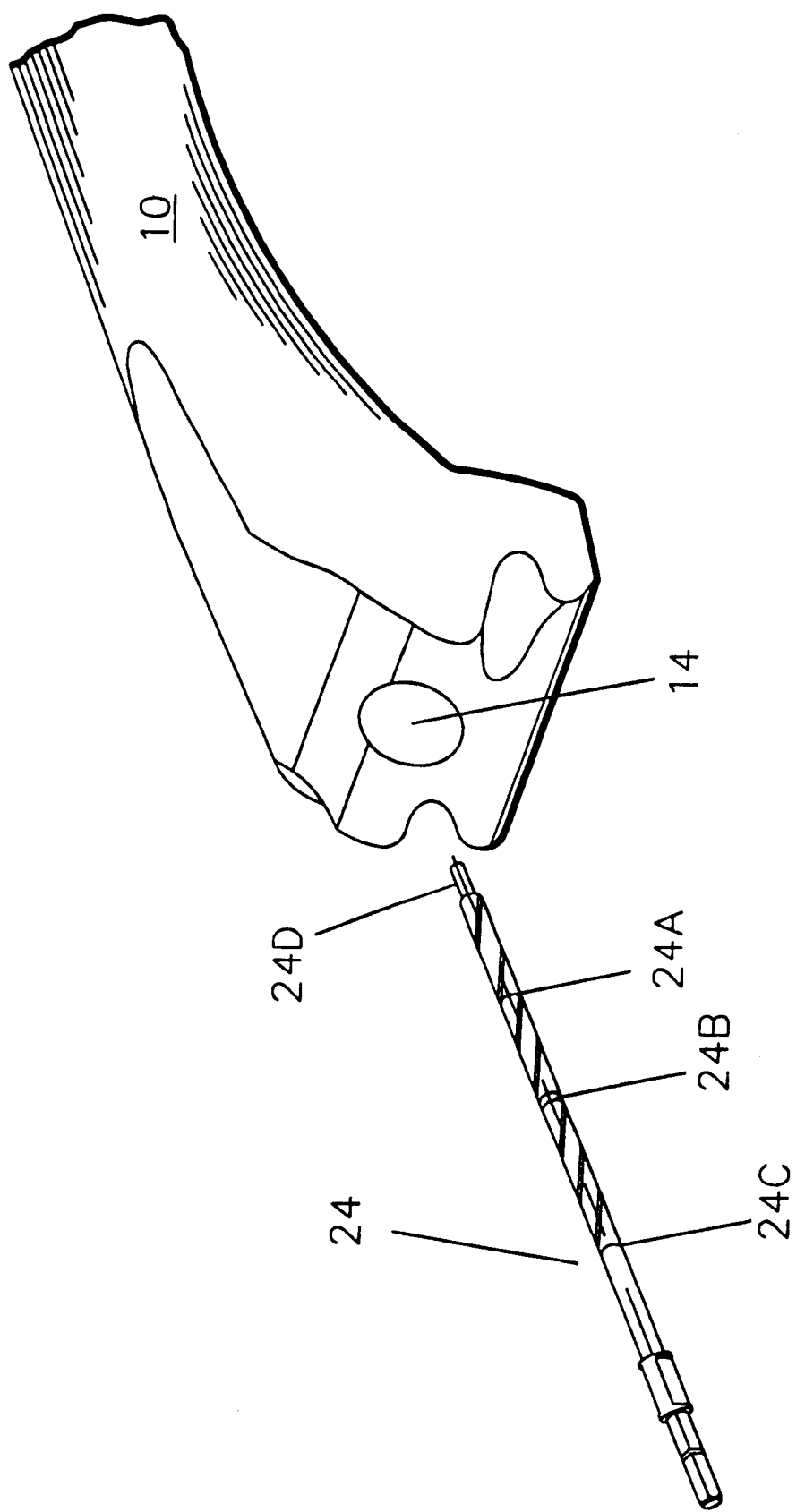

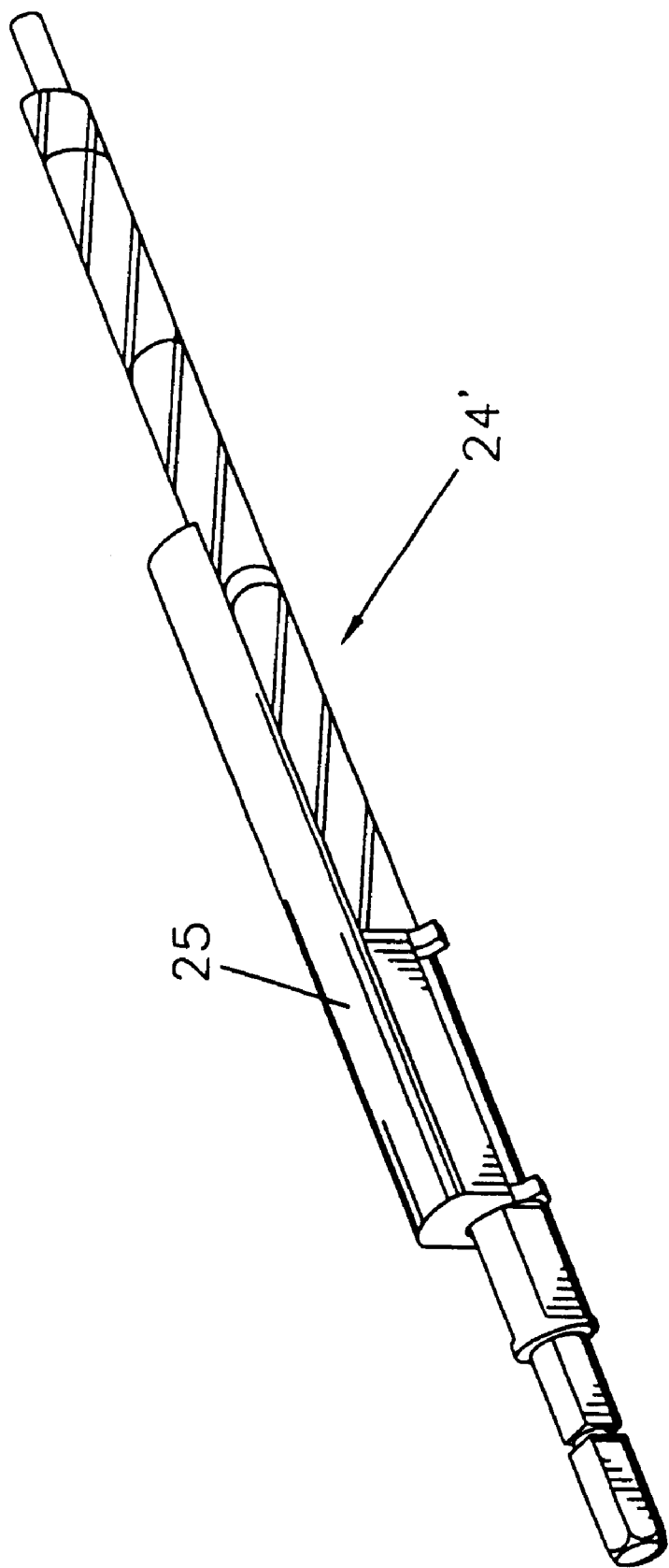

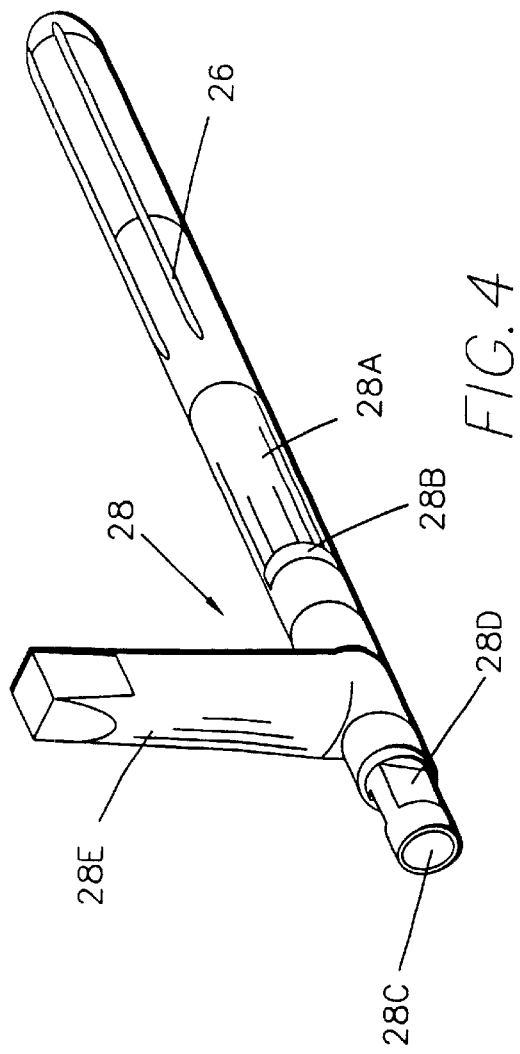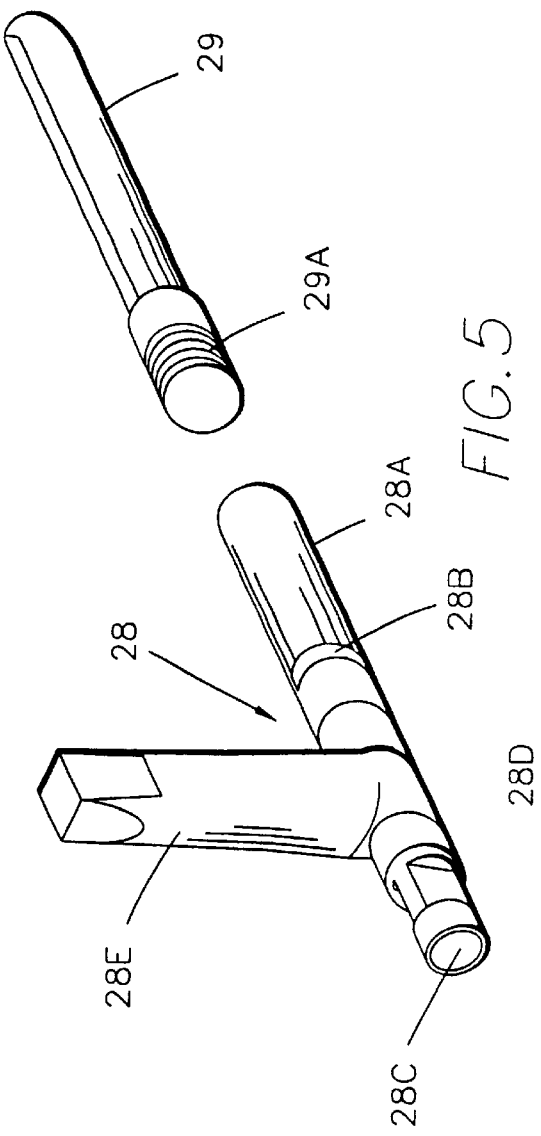

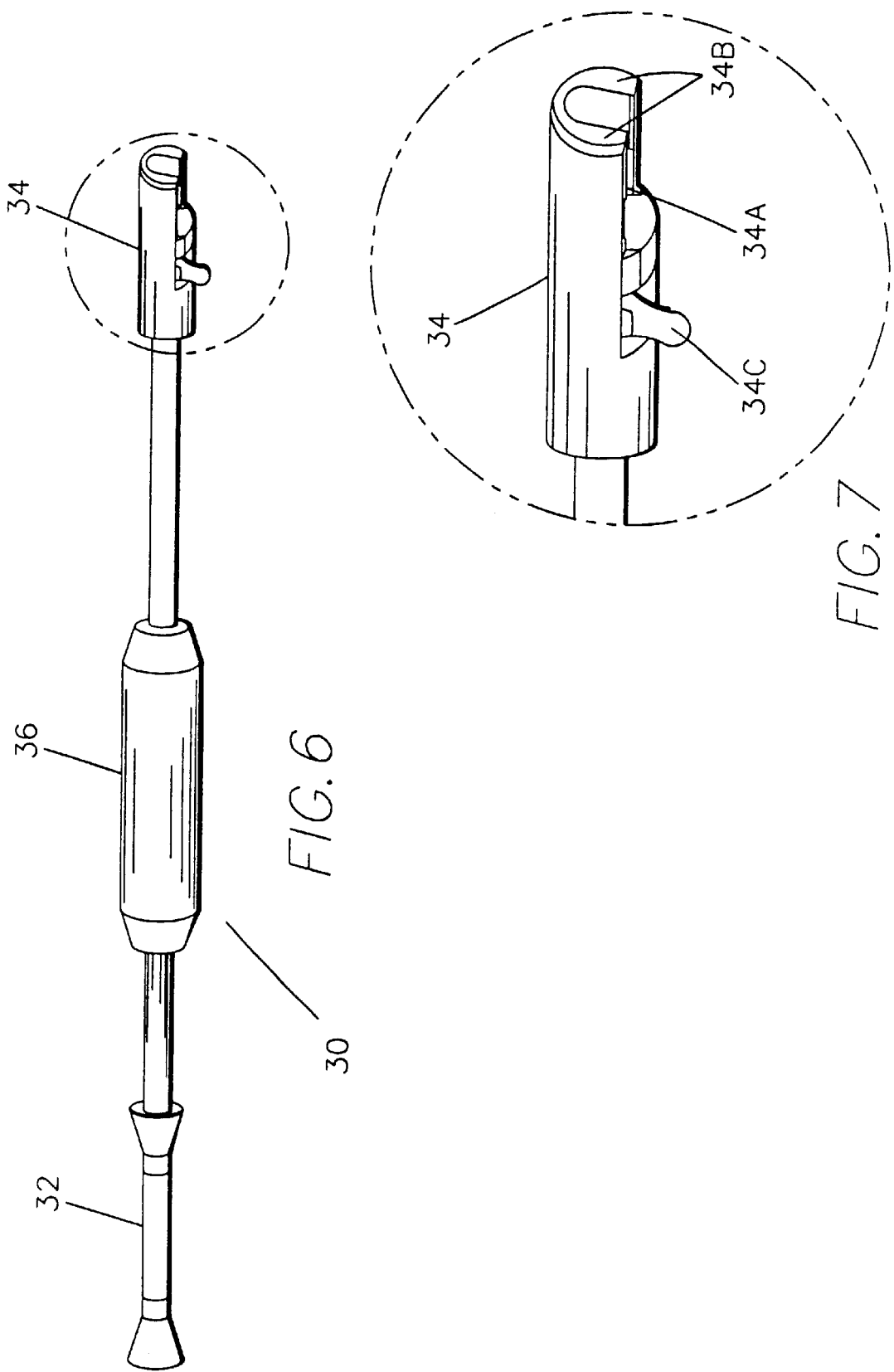

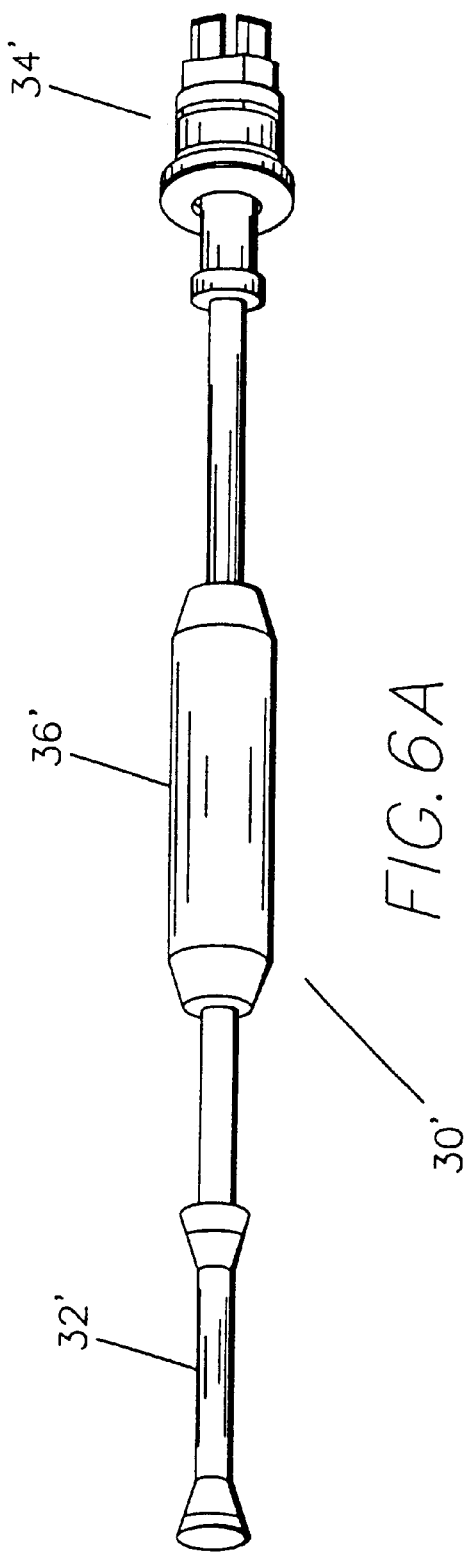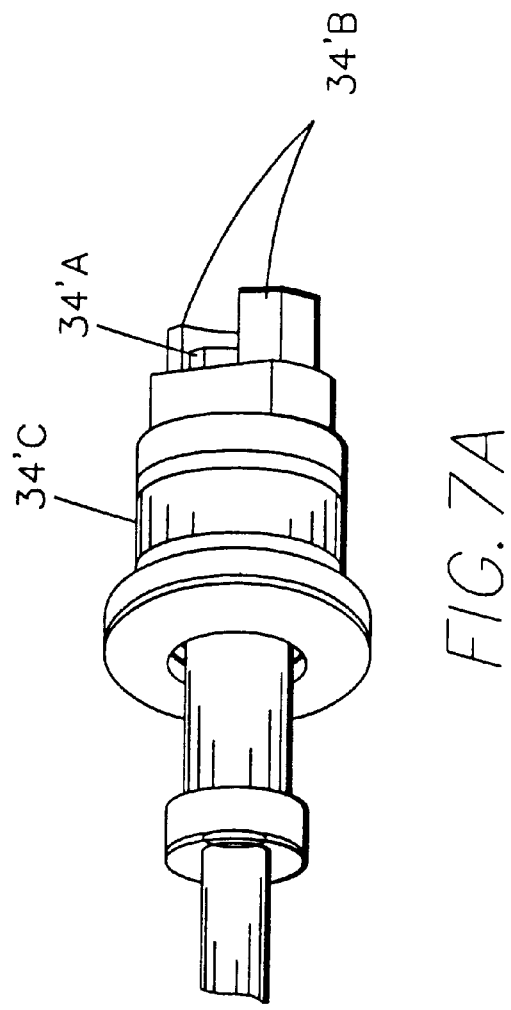
FIG.6A
FIG.7A

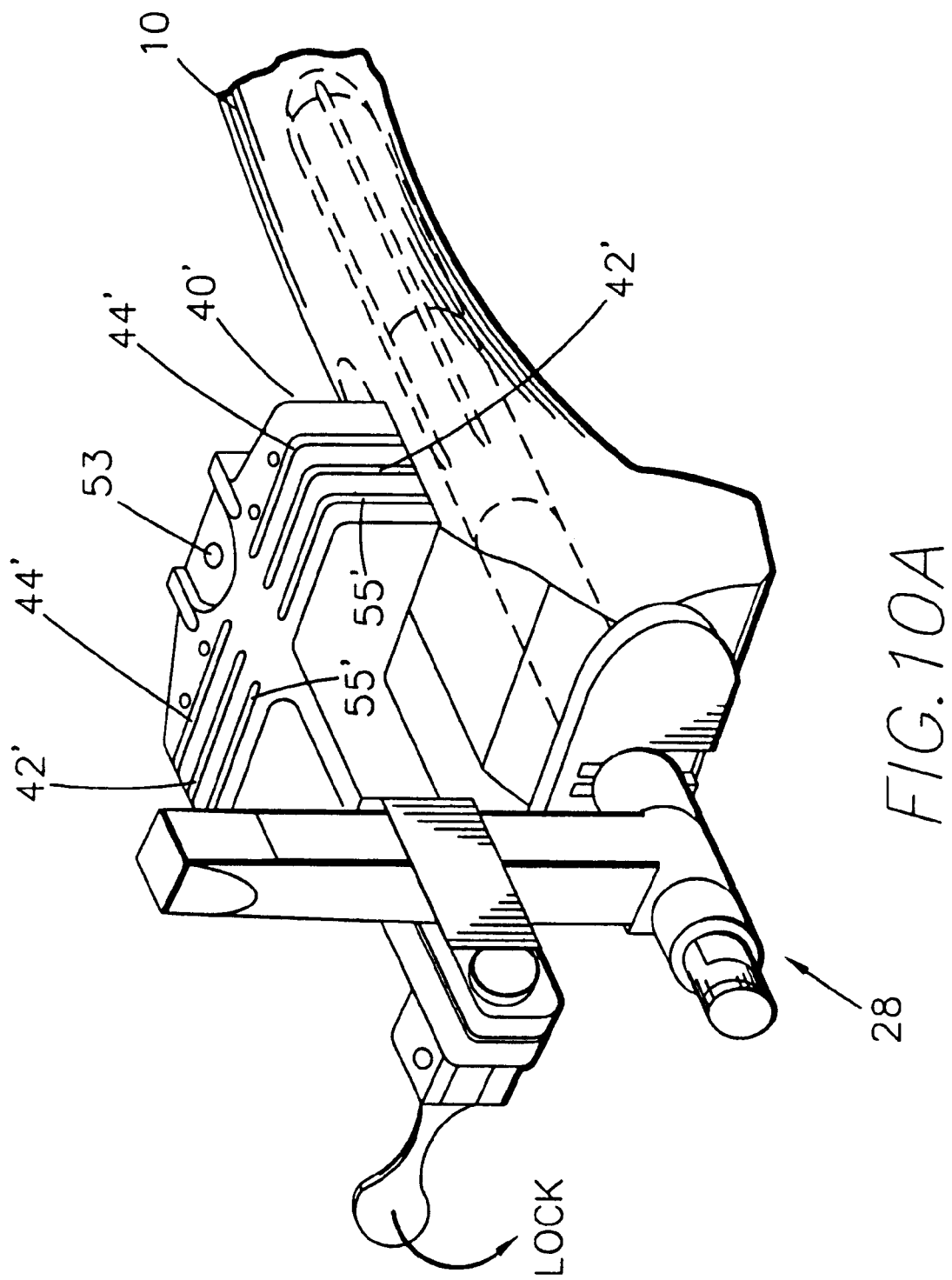

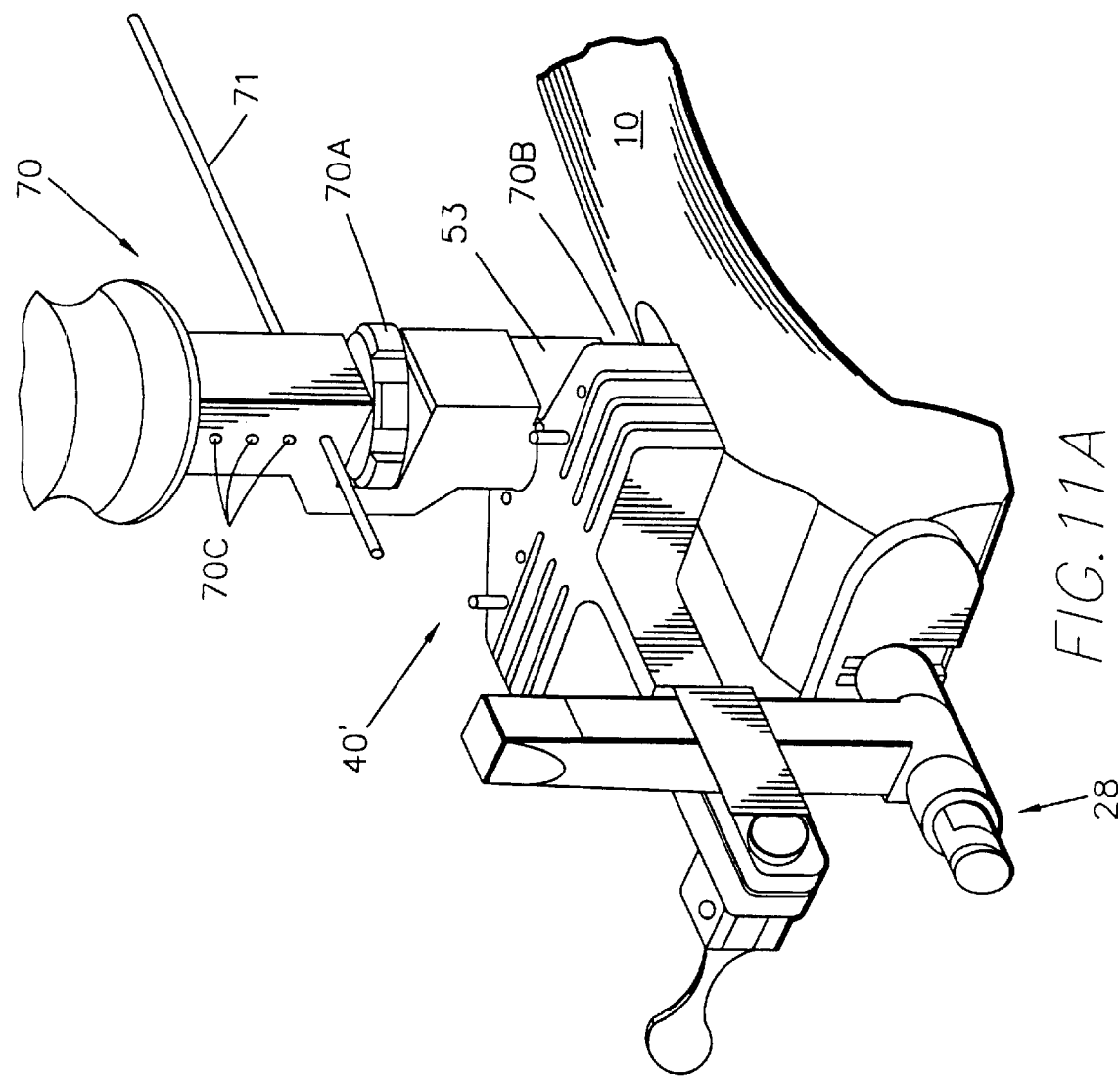

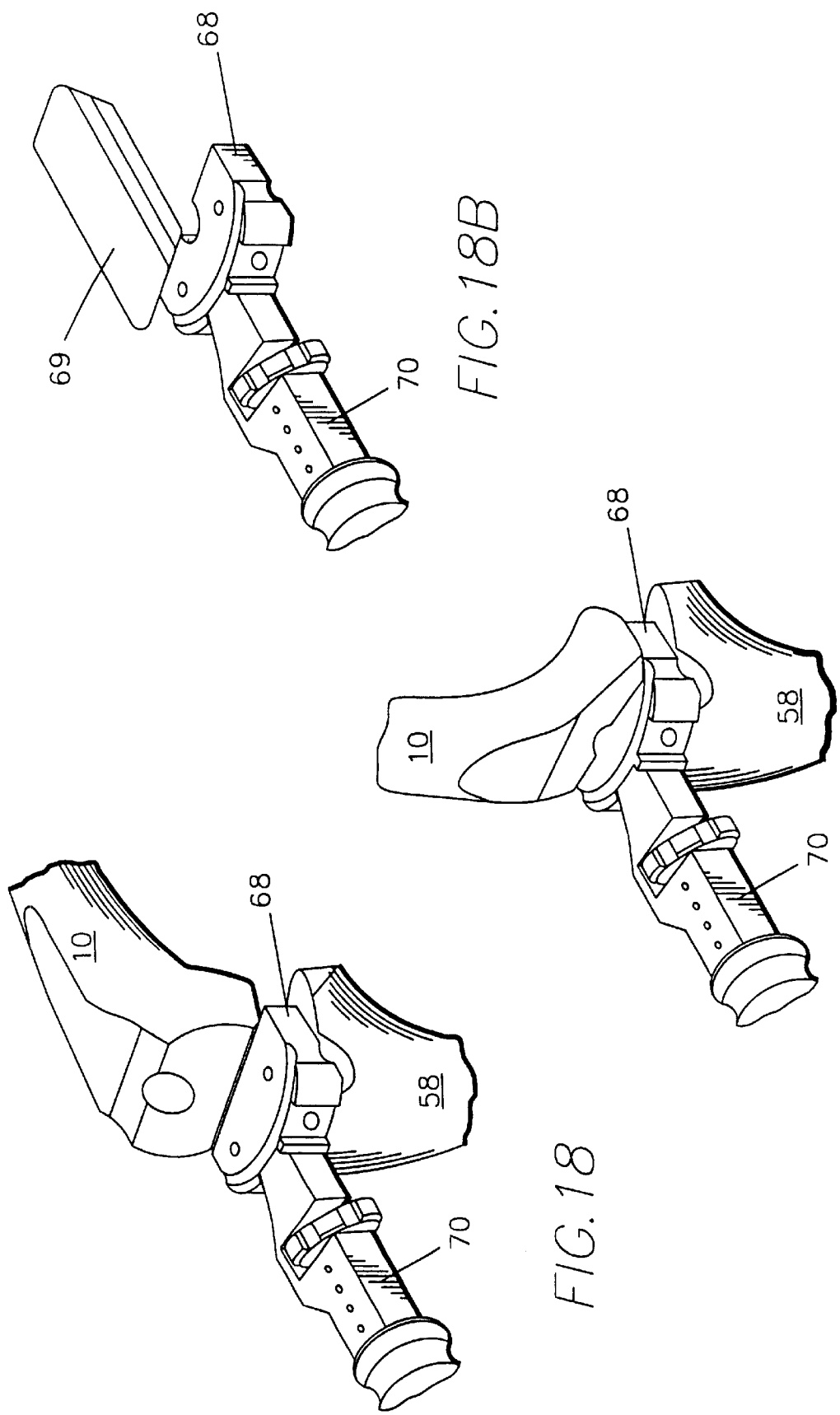

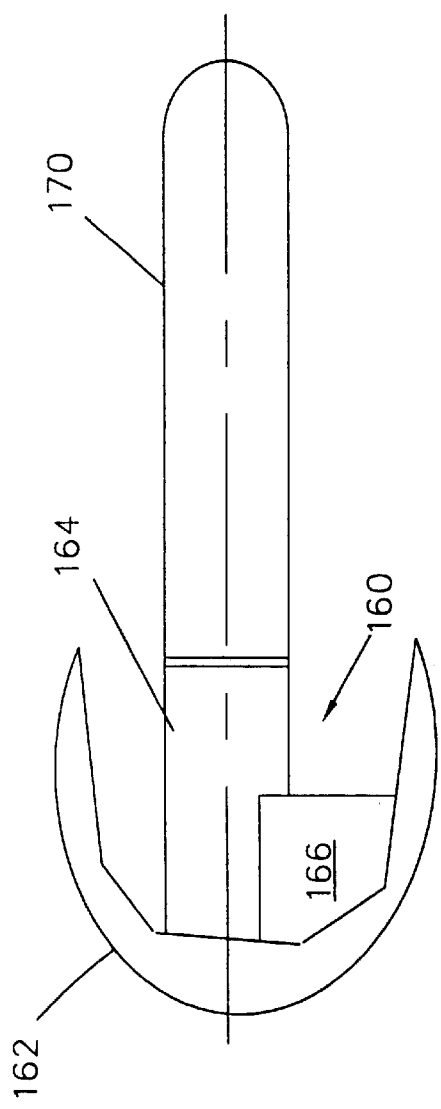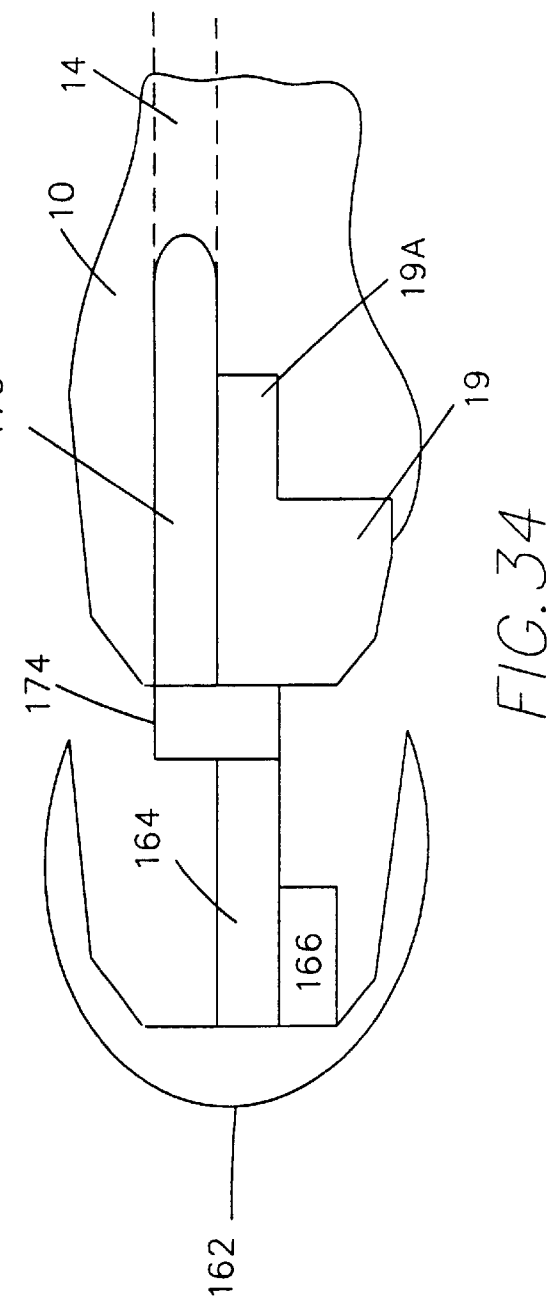

METHODS AND TOOLS FOR FEMORAL INTERMEDULLARY REVISION SURGERY

CROSS REFERENCE TO RELATED APPLICATIONS

This application is a divisional of U.S. Ser. No. 09/049,705 filed Mar. 28, 1998.

BACKGROUND of the INVENTION

1. Field of the Invention

The invention relates to methods and tools used in knee arthroplasty. More particularly, the invention relates to methods and tools used in revision surgery where an artificial femoral component is removed and replaced.

2. Brief Description of the Prior Art

Total knee arthroplasty involves the replacement of portions of the patellar, femur and tibia with artificial components. In particular, a proximal portion of the tibia and a distal portion of the femur are cut away (resected) and replaced with artificial components. As used herein, when referring to bones or other body parts, the term "proximal" means closest to the heart and the term "distal" means more distant from the heart. When referring to tools and instruments, the term "proximal" means closest to the practitioner and the term "distal" means distant from the practitioner.

There are several types of knee prostheses known in the art. One type is sometimes referred to as a "resurfacing type". In these prostheses, the articular surface of the distal femur and proximal tibia are "resurfaced" with respective metal and plastic condylar-type articular bearing components. These knee prostheses provide adequate rotational and translational freedom and require minimal bone resection to accommodate the components within the boundaries of the available joint space.

The femoral component is a metallic alloy construction (cobalt-chrome alloy or 6A14V titanium alloy) and provides medial and lateral condylar bearing surfaces of multi-radius design of similar shape and geometry as the natural distal femur or femoral-side of the knee joint.

The tibial component usually includes a distal metal base component and a proximal interlocking plastic, e.g. UHMWPE (ultra high molecular weight polyethylene), component or insert. The plastic tibial plateau bearing surfaces are of concave multi-radius geometry to more or less match the articular geometry of the mating femoral condyles. Both the femoral and tibial components are usually provided with intermedullary (IM) stem options.

After preparing the distal surface of the femur and the proximal surface of the tibia, an opening is made into the medullary canal of the femur, and an opening is made into the medullary canal of tibia. The interior surface and the IM stem of the femoral component are usually covered with a polymeric cement and the IM stem is inserted into the medullary canal of the femur until the interior surface of the femoral component meets the distal surface of the femur. The tibial component is similarly usually cemented to the proximal surface and medullary canal of the tibia.

Occasionally, the components are press fit without the use of cement. The use of cement has advantages and disadvantages. Press fit components rely on bone quality to obtain good fixation. Sometimes it is impossible to obtain good fixation with a press fit component and sometimes a press fit component will fail early because of failure of successful biological ingrowth. Cement assures good fixation but puts strain along the component stem. In addition, as described below, cement complicates the removal of a failed component.

Often, due to normal wear over time, the prosthetic knee must be replaced via a procedure known as revision surgery. When the primary cemented prosthetic is removed, the proximal surface of the tibia and the distal surface of the femur typically exhibit cavernous defects. Absent the use of bone graft, the proximal surface of the tibia and the distal surface of the femur must be carefully resected to remove cavernous defects before a replacement knee can be installed.

In addition, the intramedullary (IM) canals must be broached or reamed to remove any remaining cement or cavernous defects existing in the canals before a replacement knee can be installed. In many instances, the replacement femoral component will be provided with a posterior stabilizer and a posterior distal portion of the femur will need to be removed in order to accommodate the posterior stabilizer.

The absence of bony landmarks (removed during primary surgery) and the presence cavernous defects make extramedullary (EM) alignment of cutting jigs difficult even in cases where the primary prosthetic did not use cement.

The state of the art method for accomplishing revision arthroplasty involves the use of several cutting blocks which must be aligned with reference to the IM canal.

After the primary prosthetic is removed, the distal femur is resected with a lateral template. The medullary canal is reamed and the reamer is tapped in place with a mallet. A distal resection guide is attached to the reamer and distal resection is completed via slots in the guide. The distal resection guide is removed from the reamer and another cutting block is attached to the reamer for A/P and chamfer resections.

The rotational alignment of the femoral component is critical to ensure correct patellar tracking. Since the posterior condyles are no longer present, this cutting block must be carefully aligned relative to the femoral epicondyles where the collateral ligaments are attached.

After anterior/posterior and chamfer resections are completed, the cutting block is removed and fourth cutting block is attached to the reamer in order to accomplish intercondylar box resection. It will be appreciated that the installation and removal of the several cutting blocks makes alignment of the cutting blocks more difficult.

Following preparation of the femur, similar procedures are performed on the proximal tibia. In particular, a reamer is installed with a mallet. An anterior resection block is pinned to the tibia and a proximal portion of the tibia is resected.

The defect in the tibia is measured and the cutting guide is moved down 6 to 10 mm. A flat cut from anterior to posterior is made. A tibial template is attached to the reamer and reference marks are made with a blue pen. A flat cut and sagittal cut are made relative to the reference marks. Another template is attached to the reamer and anterior and posterior holes are drilled for securing a wedge resection guide. A wedge cut is then made. The template is replaced and aligned with the marks. A revision mask punch guide is attached to the template and a revision box chisel is used to prepare for a stem. The femur and tibia are now in condition for trialing.

Trialing is accomplished by attaching a femoral trial augmentation and stem extension, tightening the stem extension into a stem boss, positioning a trial augmentation block on the underside of a trial plate, inserting bolts through the top of the plate and tightening the bolts, inserting a constrained modular post into the bearing trial, placing the constrained femoral trial, and stemmed tibial trial into the joint space. After successful trialing, the femoral and tibial components are installed.

Those skilled in the art will appreciate that revision surgery is difficult because (1) the type and location of cavernous defects make it difficult to match the exterior surfaces of the tibia and femur to the interior surfaces of the prosthetic, (2) the femur and tibia must be resected with reference to the IM canal, and (3) the use of multiple templates and guides during the course of the procedure makes it very difficult to keep all the cuts in proper alignment relative to the IM canal.

SUMMARY OF THE INVENTION

It is therefore an object of the invention to provide methods and tools for performing IM revision surgery.

It is also an object of the invention to provide tools for IM revision surgery which maintain proper alignment with the IM canal while multiple resection cuts are made.

It is another object of the invention to provide methods for performing IM revision surgery in which a minimum number of tools are used.

It is still another object of the invention to provide methods and tools which enhance the accuracy of IM revision surgery and enhance the stability of the revision implant.

In accord with these objects which will be discussed in detail below, the IM revision tools of the present invention include reamers with depth markings and/or depth stops, an impactor-extractor with a distal coupling for attaching to other tools which are inserted into and removed from the IM canal, a resection guide tower to which a cutting block is accurately attached and which includes a notch which serves as both a witness mark and a holder for a femoral or tibial collar, a selection of different sized stems attachable to the guide tower, a selection of different sized femoral and tibial collars, a reversible cutting block with a quick-connect clamp attachable to the guide tower for resecting the distal femur, a right and left cutting block with quick-connect clamp attachable to the guide tower for resecting the proximal tibia, a selection of spacer blocks for measuring the space between the tibia and femur to determine the thickness of the tibial component to be installed, an all-in-one cutting guide for preparing the femur, a set of 5 and 10 mm trial wedges, a trial stem valgus adapter, femoral sizing indicators which include indications of anterior/posterior offset, a posterior stabilizer box cutting template which is attachable to the all-in-one cutting guide, and anterior/posterior offset adapters for attaching the femoral component to the IM stem. The tools according to the invention are modular and can also be used in primary knee arthroplasty with or without IM fixation.

The methods according to the invention include removing the primary femoral component, reaming an appropriate depth of the femoral IM canal with a reamer of appropriate diameter, selecting a tool stem (trial stem) of appropriate length and diameter, attaching the guide tower to the tool stem, inserting the tool stem into the femoral IM canal, attaching the impactor/extractor to the proximal end of the tool stem and impacting the stem into the IM canal (or optionally impacting the stem with a mallet), optionally attaching a stop to the tool stem prior to impacting, attaching the reversible cutting block to the tool stem resecting the distal femur, removing the cutting block from the tool stem and removing the tool stem with the impactor/extractor, repeating the procedure with respect to the proximal tibia using one of the left or right tibial cutting blocks, sizing the distal femur and the space between the femur and tibia at flexion and extension, inserting a tool stem into the femoral IM canal, attaching an all-in-one cutting block of appropriate size to the tool stem, optionally inserting a 5 or 10 mm spacer to the distal side of the cutting block before attaching to the tool stem, referencing the rotational alignment of the all-in-one cutting block to the posterior condyles (if present), or aligning the all-in-one cutting block parallel to the transepicondylar axis with the aid of a spacer block, attaching a sizing indicator to the all-in-one cutting block to confirm the cutting block size, inserting pins through the all-in-one cutting block and into the distal femur, making the anterior cut of the femur using the all-in-one cutting block, optionally attaching a stabilizer with an anterior reference plate which is pinned to the anterior of the femur, making the chamfer and posterior cuts using the all-in-one cutting block, drilling through guides in the all-in-one cutting block to locate the position of the posterior stabilizer box, attaching the posterior stabilizer box template to the all-in-one cutting block, inserting the posterior stabilizer box chisel through the template to remove bone for the posterior stabilizer box.

The methods and tools of the invention provide accurate location of bone cuts so that the revision prosthetic is correctly oriented relative the IM canal and the bone cuts. Additional objects and advantages of the invention will become apparent to those skilled in the art upon reference to the detailed description taken in conjunction with the provided figures.

BRIEF DESCRIPTION OF THE DRAWINGS

FIG. 3 is a view similar to FIG. 2 illustrating instruments used in the first step in the method of the invention;

FIG. 3A is a perspective view of an alternate embodiment of the reamer shown in FIG. 3;

FIG. 4 is a perspective view of a resection guide tower attached to a trial stem;

FIG. 5 is a perspective view of the guide tower removed from the trial stem and ready to be attached to an optional long IM rod;

FIG. 6 is a perspective view of an impactor/extractor;

FIG. 6A is a perspective view of an alternate embodiment of the impactor/extractor shown in FIG. 6;

FIG. 7 is an enlarged detail of a portion of FIG. 6;

FIG. 7A is an enlarged detail of a portion of FIG. 6A;

FIG. 10A is an alternate embodiment of the cutting block of FIG. 10;

FIG. 11A is a view similar to FIG. 11 showing the cutting block of FIG. 10 A with optional EM alignment indicator tools attached;

FIGS. 18 and 18A are broken perspective views illustrating tools for sizing of the gap between the femur and the tibia in flexion and extension;

FIG. 18B is a broken perspective view of the tool shown in FIGS. 18 and 18A with an optional wedge cut spacer block;

FIG. 33 is a side elevational view of a femoral component with a posterior stabilizer box;

FIG. 34 is a side elevational view of a femoral component with a posterior stabilizer box and an anteriorly offset stem;

DETAILED DESCRIPTION

Figure 2:
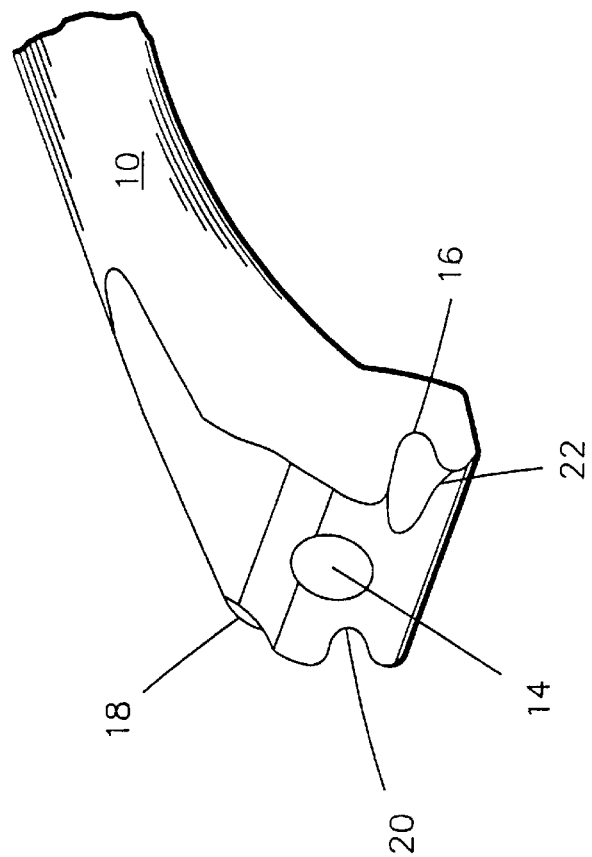
FIG. 2 is a broken perspective view of the distal femur after removal of the primary prosthetic component.
Figure 1:
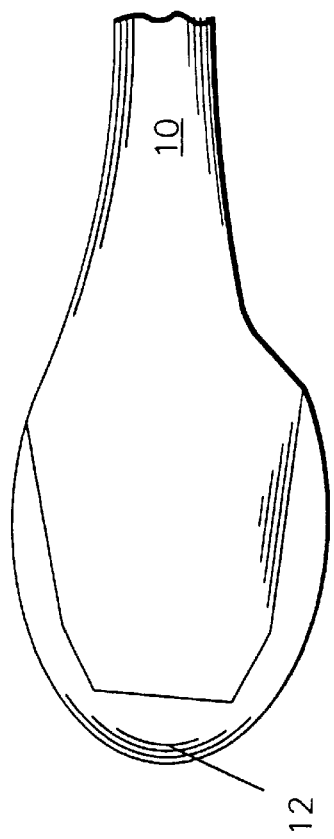
FIG. 1 is a broken side elevational view of a distal femur with a primary prosthetic component.

FIG. 1 illustrates the distal portion of the femur 10 and a total condylar femoral component 12. If the component 12 is a primary component, it may or may not have a stem depending on the choice of the surgeon during primary surgery. If the component 12 is a revision component, it will have a stem which extends into the IM canal (14 in FIG. 2) of the femur 10.

Once the component 12 is removed, all loose cement and underlying fibrous membrane are removed. A meticulous debridement should be performed with the aid of high-speed lavage. After all foreign material is removed, the soft tissue is examined and scarred tissues are removed. Generally, the anterior cruciate is sacrificed. If the revision implant will have a posterior stabilizer box, the posterior cruciate ligament may also be removed.

Upon removal of the component 12 and all the foreign material, the femur 10 will likely exhibit cavernous defects, e.g. 16, 18, 20, 22 on the bone which was covered by the component 12. These defects are the result of cement used to install the component 12. When the component 12 is removed (usually with the aid of an ultrasonic knee osteotomes to disrupt the cement interface) some of the cement remains firmly affixed to the component and the underlying bone, and portions of bone are removed with the component. For this reason, among others, the distal surface of the femur can not be used as a reference for installing a new prosthetic. In order to properly locate the new prosthetic, the IM canal 14 must be used as the reference.

According to the invention, after the removal of the component 12, the IM canal 14 is located so that it can be reamed. If the component 12 did not have a stem, an opening in the canal 14 is first made with a ⁵⁄₁₆" intercondylar stepped drill (not shown). The entry point for the drill is preferably 5–10 mm anterior to the origin of the posterior cruciate ligament (also not shown).

Turning now to FIG. 3, once the IM canal 14 has been located, a reamer 24 of appropriate diameter is selected. If the canal has not been previously prepared, an 8 mm diameter reamer should be used to start and progressively larger reamers used until cortical contact is achieved. (Clinical evidence suggests that an 8 mm diameter IM rod may be inserted into the canal without any reaming. If so, such a rod should be inserted prior to reaming in order to establish the mechanical axis of the IM canal.) If the component 12 which was removed had a stem, reaming should begin with a reamer 2 mm smaller in diameter than the stem which was removed.

The reamer 24, according to the invention, is provided with three depth markings 24*a*, 24*b*, and 24*c*. These markings correspond respectively to the length of the boss of the stemmed components, an 80 mm depth, and a 155 mm depth. In addition, the reamer 24 is provided with a bullet tip 24*d* which is 2 mm smaller in diameter than the cutting edges of the reamer. An alternative embodiment of a reamer 24' is shown in FIG. 3A. The reamer 24' is substantially the same as the reamer 24 but is provided with a plurality of snap-on stops 25 which are used in lieu of or in addition to depth markings.

According to the apparatus of the invention, reamers of different diameter are provided, the smallest being 8 mm, each having a 1 mm larger diameter. Each of the reamers is fully fluted, has the bullet tip, and the depth markings or stops described above. According to the method of the invention, the IM canal is progressively reamed with a 9 mm reamer, then a 10 mm reamer, then an 11 mm reamer, etc. until cortical contact is achieved. Progressive use of the reamers according to the invention assures that the correct anatomic axis of the IM canal is achieved, even in a bowed canal.

Referring now to FIGS. 4 and 5, based on the diameter and reaming depth of the last IM reamer used, an appropriate trial stem 26 is chosen for attachment to the cutting block tower 28. The tower 28 has a boss 28*a* with a pair of surface grooves 28*b*, a stem 28*c* with a pair of surface grooves 28*d*, and an upstanding shaft 28*e* therebetween. The boss 28*a* has interior threads (not shown) and the stem 26 is provided with engaging exterior threads (not shown). The boss 28*a* has a diameter of 15 mm and several stems 26 of different diameter are provided for attachment to the tower 28.

There are situations which will require the use of an implant having a stem smaller than 15 mm in diameter or which will require an implant having no stem. In these cases, the IM will be reamed 15 mm in diameter to the depth of the boss 28*a* (to the first depth indicator 24*a* in FIG. 3) in order to accommodate the boss of the tower 28 as well as the boss of the implant (FIG. 33).

In order to provide an IM reference in these situations, an IM rod 29 with a threaded end 29*a* may be attached to the boss 28*a* of the tower 28. According to the invention, an 8 mm×255 mm IM rod is provided with a threaded end for coupling to the cutting block tower as shown in FIG. 5. In addition, according to the invention, IM rods 80 mm and 155 mm in length are also provided for use in situations where the femur is extremely bowed, or an obstruction of the IM canal is present.

As shown in FIGS. 4 and 5, the tower 28 is provided with grooves 28*b* on the boss 28*a* and is provided with a stem 28*c* having slots 28*d*. The grooves 28*b* are used to locate the insertion depth of the tower as described in more detail below with reference to FIGS. 8 and 9. The stem 28*c* and the slots 28*d* are provided so that the tower 28 may be removably coupled to an impactor/extractor tool which is shown and described with reference to FIGS. 6 and 7.

An impactor/extractor tool 30 according to the invention is shown in FIGS. 6 and 7. The tool 30 has a proximal handle 32, a distal coupling 34, and a sliding mass 36. The coupling 34 has a slot 34*a* which is dimensioned to receive the stem 28*c* of the tower 28, and a pair of distal shoulders 34*b* which are dimensioned to fit into the slots 28*d* of the stem 28*c*. A spring loaded latch 34*c* is located adjacent to the slot 34*a*.

Figure 8:
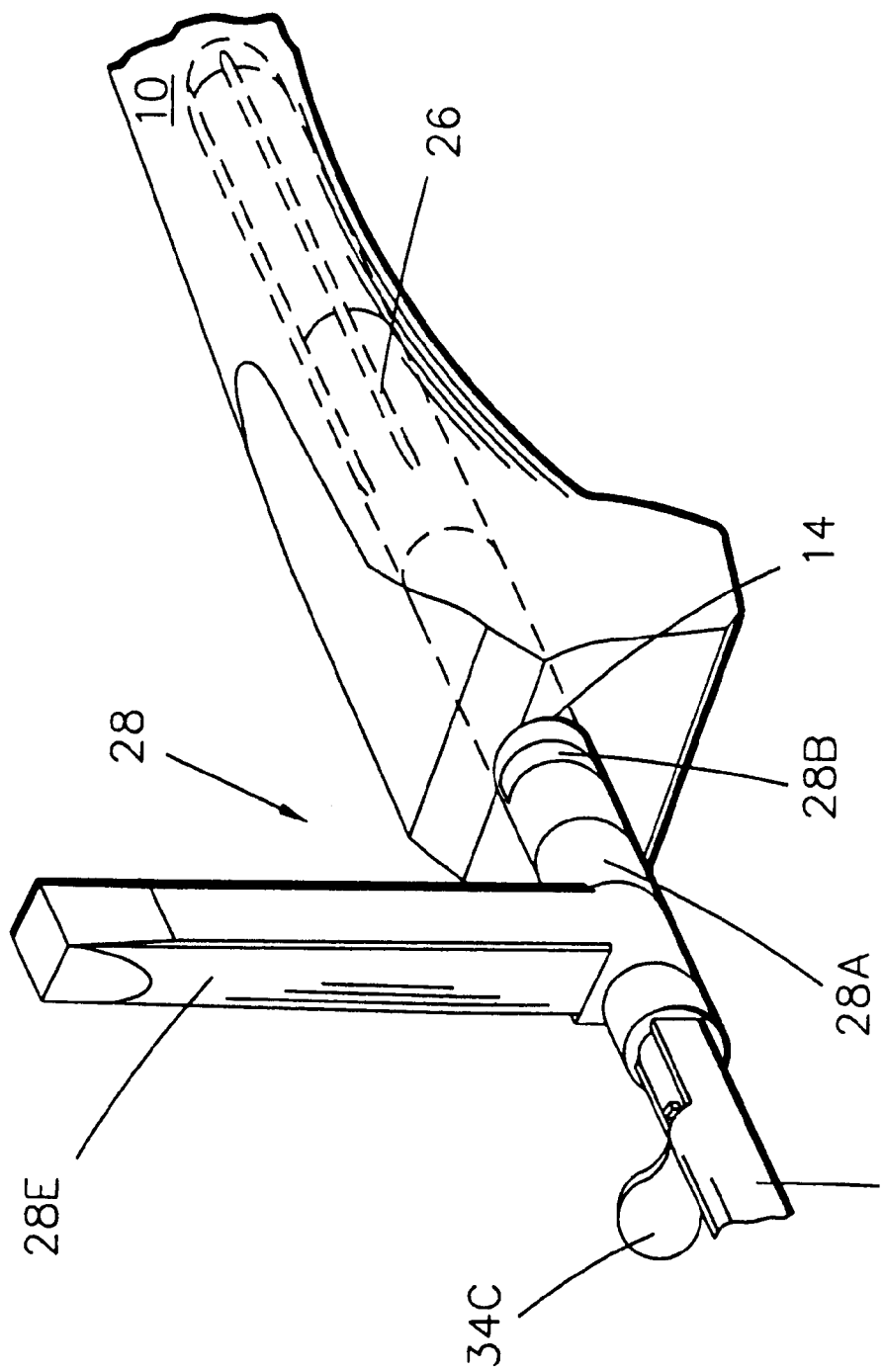
FIG. 8 is a broken perspective view of the guide tower and trial stem assembly coupled to the impactor/extractor and inserted into the IM canal of the femur.

The tool 30 is removably attached to the tower 28 as shown in FIG. 8. The stem 26 of the tool 28 is then inserted into the IM canal 14 and the sliding mass 36 of the tool 30 is slid distally. The force of the accelerated mass 36 impacts the coupling 34 and drives the stem 26 of the tower 28 into the IM canal 14. If necessary, the mass is slid several times until the stem 26 is fully inserted into the IM canal 14. After the tower 28 is installed, the impactor/extractor tool 30 is uncoupled from the tower 28.

FIGS. 6A and 7A show an alternate embodiment of an impactor/extractor 30Æ according to the invention where similar reference numerals refer to similar parts. The tool 30' has a different type of coupling 34' which utilized a spring loaded collar 34'*c* which slides over the slot 34'*a* and shoulders 34'*b*.

As shown in FIG. 8, the grooves 28*b* on the boss 28*a* of the tower 28 serve as witness marks for the proper placement of the tower. In particular, the tower stem 26 and boss 28*a* are inserted into the IM canal 14 until the grooves 28*b* are in line with the most prominent bony aspect of the distal femur. This position will result in a 2 mm distal clean-up cut as described below with reference to FIGS. 10 and 11.

Figure 9:
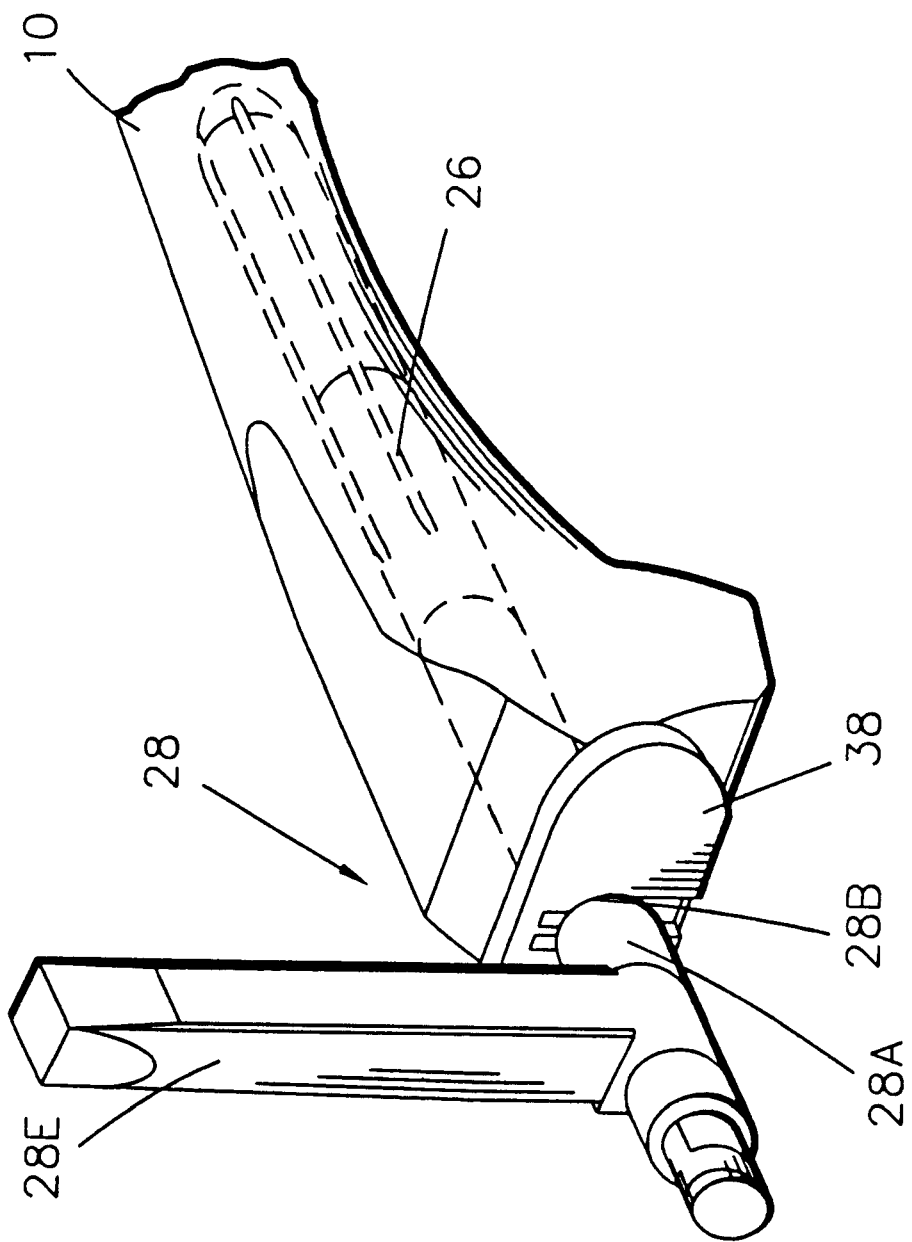
FIG. 9 is a broken perspective view of the guide tower and trial stem assembly coupled to an optional collar and inserted into the IM canal of the femur.

In situations where the canal opening is enlarged and does not provide adequate support or a good reference point to seat the tower boss 28*a*, a small or medium sized femoral collar 38, shown in FIG. 9, is attached to the boss 28*a* by engaging the grooves 28*b*. In addition to stabilizing the tower 28, the collar 38 also provides a means for preliminary sizing of the femur. It will be appreciated that the collar 38 may be used in all cases (regardless of the condition of the IM canal) in order to assure proper placement of the tower 28 and preliminary sizing of the femur.

Figure 10:
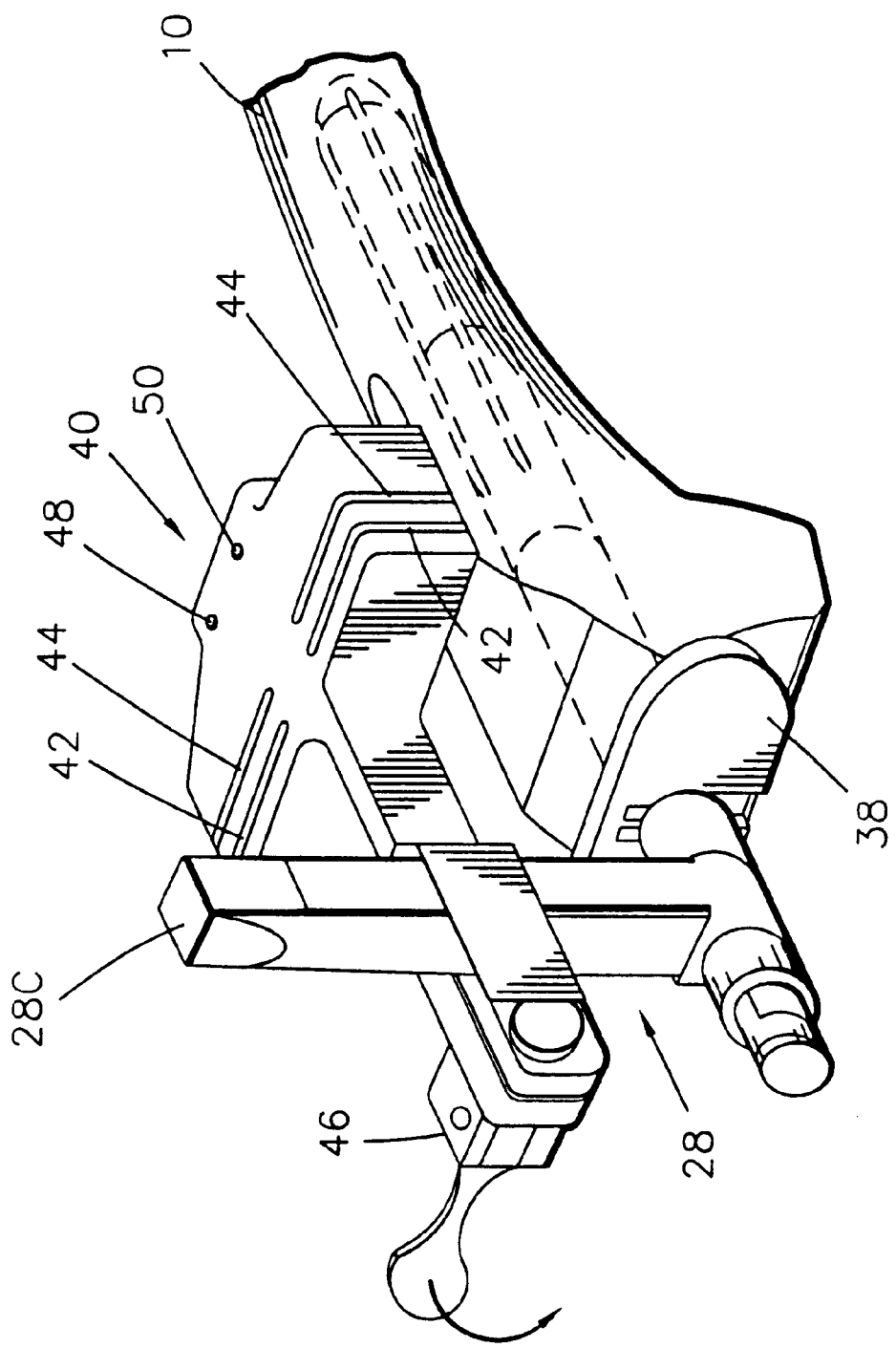
FIG. 10 is a broken perspective view of an "open face" reversible cutting block attached to the guide tower.

Once the tower 28 is properly installed, the femoral cutting block 40 is attached to the tower 28 as shown in FIG. 10. The cutting block 40 has two 5 mm cutting slots 42 and two 10 mm cutting slots 44 which are aligned to the valgus angle [alpha] of the implant stem (FIGS. 33 and 34). The cutting block 40 is attached to the upstanding shaft 28*e* of the tower 28 by means of a cam lock 46.

Figure 11:
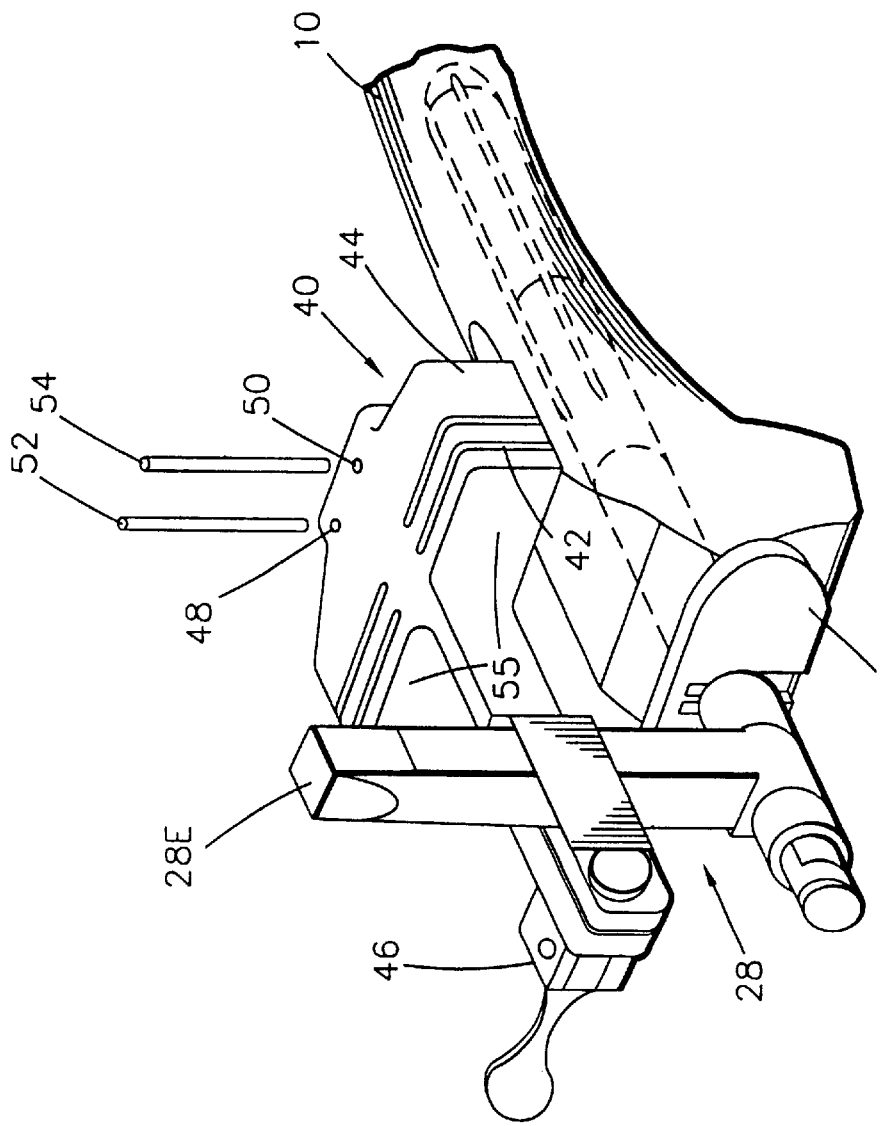
FIG. 11 is a view similar to FIG. 10 showing optional pins used to secure the cutting block to the anterior femur.

It will be appreciated that the femur cutting block 40 is reversible so it can be used with left or right knees and still achieve the proper valgus angle. The cutting block 40 is also provided with a pair of drill holes 48 and 50 for further securing the cutting block to the femur, As seen in FIG. 11, two ⅛" drill bits 52, 54 are inserted through the drill holes 48, 50 to secure the cutting block 40 before the clean-up cut is made.

With the cutting block so secured, a 2 mm clean-up cut is made using the proximal surface 55 of the cutting block as a guide. The surface 55 is parallel to the slots 42, 44 and thus exhibits the same valgus angle. After the clean-up cut is made, the cutting block 40 and the tower 26 are removed from the femur 10 if no wedge cuts will be made. In some situations, a 5 mm or 10 mm distal femoral wedge cut will be made.

Removal of the cutting block 40 is effected by removing the drill bits 52, 54, unlocking the cam lock 46, and sliding the cutting block off the shaft 28*e*. The tower 28 is removed from the IM canal using the impactor/extractor tool 30 shown in FIG. 6.

Specifically, the tool 30 is attached to the tower 28 as described above and the mass 36 is slid proximally toward the handle 32. The force of the accelerated mass 36 impacting on the handle 32 is translated to the distal coupling 34 of the tool 30 and pulls on the tower 28, withdrawing it from the IM canal. At this point in the procedure, before further preparation of the femur can be accomplished, the tibia must be prepared.

FIGS. 10A and 11A show an alternate embodiment of a femoral cutting block 40' where similar reference numerals refer to similar parts. The cutting block 40' is provided with a pair of 2 mm clean-up cutting slots 55' and a distal coupling 53. The coupling 53 mates with a handle 70 as shown in FIG. 11A. The handle 70 has a rotatable thumb wheel 70a for rotating a threaded connector 70b and has a plurality rod receiving apertures 70c. The handle 70 has several functions as will be described herein. When used as shown in FIG. 11A, the handle 70 is attached to the coupling 53 and a rod 71 is inserted into one of the apertures 70c. The assembly shown in FIG. 11A permits an optional visual EM alignment inspection prior to making any cuts.

Figure 12:
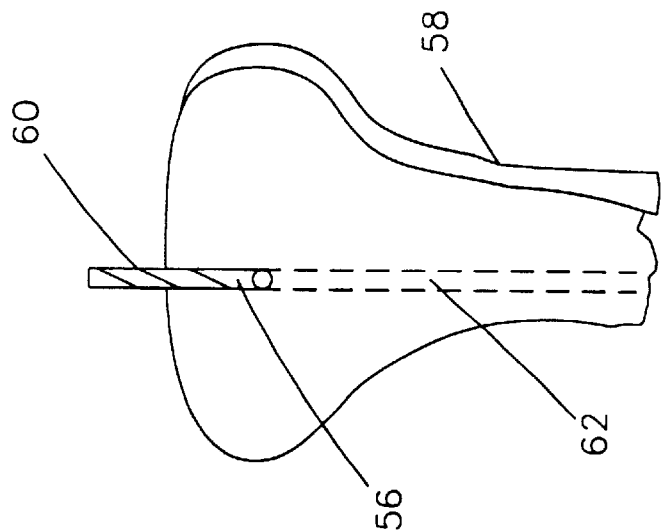
FIG. 12 is a broken perspective view illustrating initial preparation of the tibia by drilling to locate the IM canal.
Figure 13:
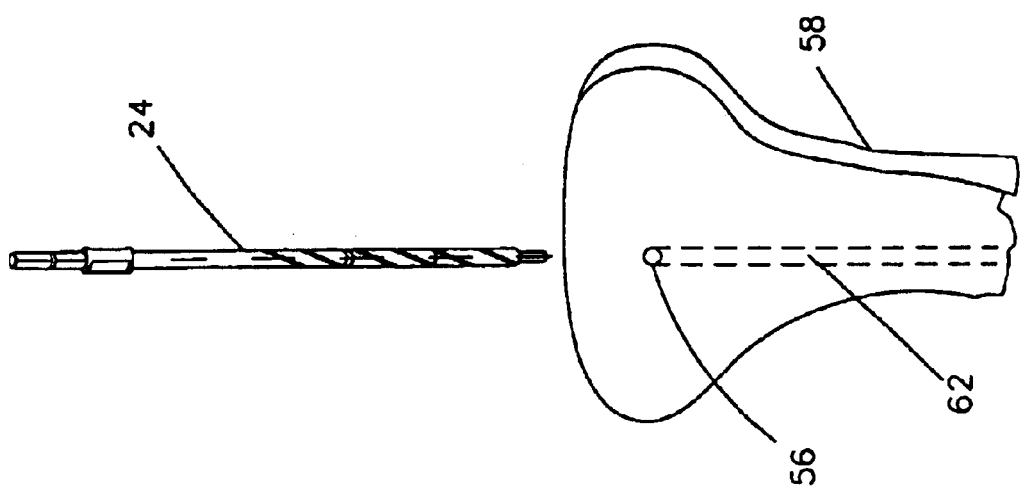
FIG. 13 is a view similar to FIG. 12 illustrating the reaming of the IM canal.

Turning now to FIGS. 12 and 13, after removing the previous tibial component (not shown), an opening 56 is made in the proximal tibia 58 with a 5/16" intercondylar stepped drill 60 to locate the medullary canal 62. Once the canal 62 has been located, a reamer 24 of appropriate diameter is selected.

If the canal has not been previously prepared, an 8 mm reamer should be used to start and progressively larger reamers used until cortical contact is achieved. (Clinical evidence suggests that an 8 mm rod may be inserted into the canal without any reaming. If so, such a rod should be inserted prior to reaming in order to establish the mechanical axis of the canal.) If the component which was removed had a stem, reaming should begin with a reamer 2 mm smaller in diameter than the stem which was removed and continue progressively until cortical contact is achieved. The reamer 24 is the same type as described above with respect to the femoral IM canal.

Figure 14:
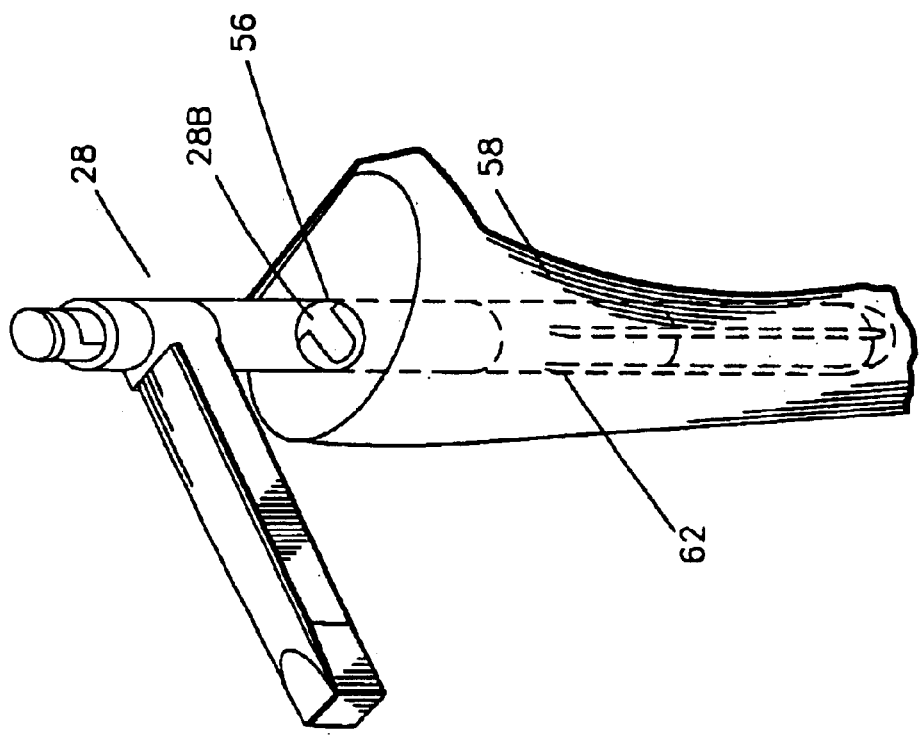
FIG. 14 is a broken perspective view of the guide tower and trial stem assembly inserted into the IM canal of the tibia.
Figure 16:
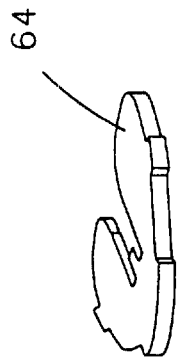
FIG. 16 is a perspective view of the collar of FIG. 15.
Figure 15:
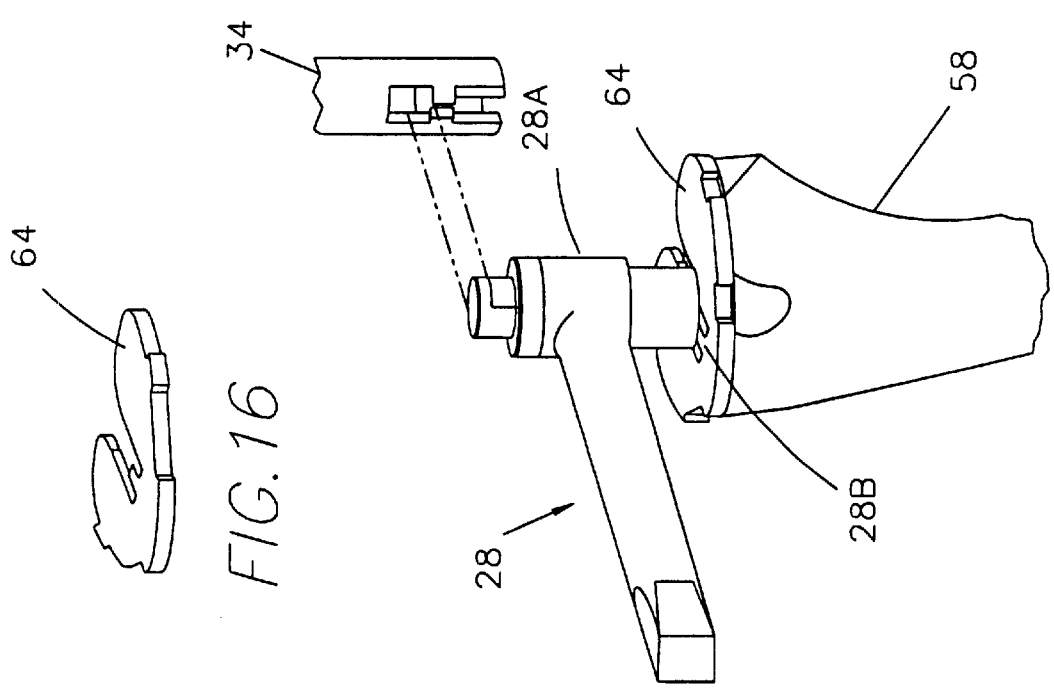
FIG. 15 is a broken perspective view of the guide tower and trial stem assembly coupled to an optional collar and inserted into the IM canal of the tibia and also illustrating the coupling to the impactor/extractor to the guide tower.

After the tibial canal is prepared, a resection guide tower 28 of the same type as described above is installed as shown in FIGS. 14 and 15. In situations where the canal opening is enlarged and does not provide adequate support or a good reference point to seat the tower, a tibial collar 64, shown in FIG. 16, is attached to the boss 28a by engaging the grooves 28b. The tibial collar 64 is similar to the femoral collar 38 described above except that it is shaped and dimensioned to cover the tibial plateau.

In addition to stabilizing the tower, the collar 64 aids in preliminary sizing of the tibia. The tower 28 is installed in the tibial IM canal with the aid of the impactor/extractor tool in a manner similar to that described above with reference to the installation of the tower in the femoral IM canal.

Figure 17:
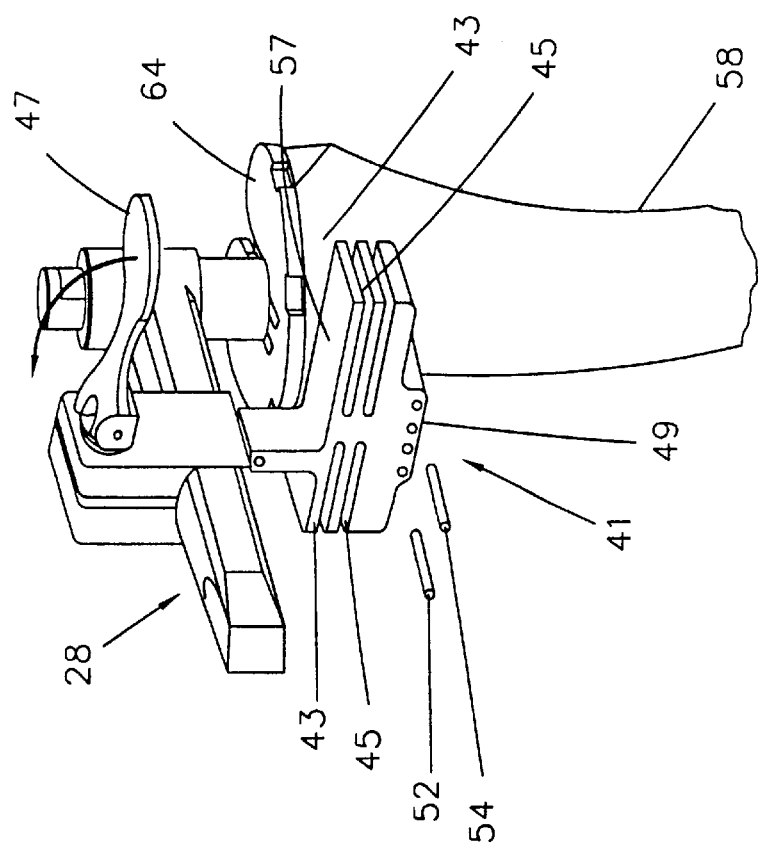
FIG. 17 is a broken perspective view of a right tibial cutting block attached to the guide tower and the optional pins used to secure the cutting block to the anterior tibia.

Once the tower 28 is properly installed, the tibial cutting block 41 (which is provided in separate left and right versions) is attached to the tower 28 as shown in FIG. 17 by means of the cam lock 47 and the two ⅛" drill bits 52, 54 inserted into holes 49. With the cutting block so secured, a 2 mm clean-up cut is made using the proximal surface 57 of the cutting block as a guide. Three degrees of posterior slope is built into the cutting block and this is why separate left and right cutting blocks are provided. Slots 43 and 45 are provided for 5 mm and 10 mm wedge cuts. After the clean-up cut and wedge cuts (if desired) are made, the cutting block 40 and the tower 26 are removed from the tibia 58. The removal of the cutting block and tower is effected in the same manner as removal from the femur described above.

In situations where a tibial component without a stem will be used and the surgeon does not wish to ream the tibial IM canal, an 8 mm rod (29 in FIG. 5) may be attached to the tower 28 and used in the same manner as described above with respect to installing the tower in the femoral IM canal.

Figure 17A:
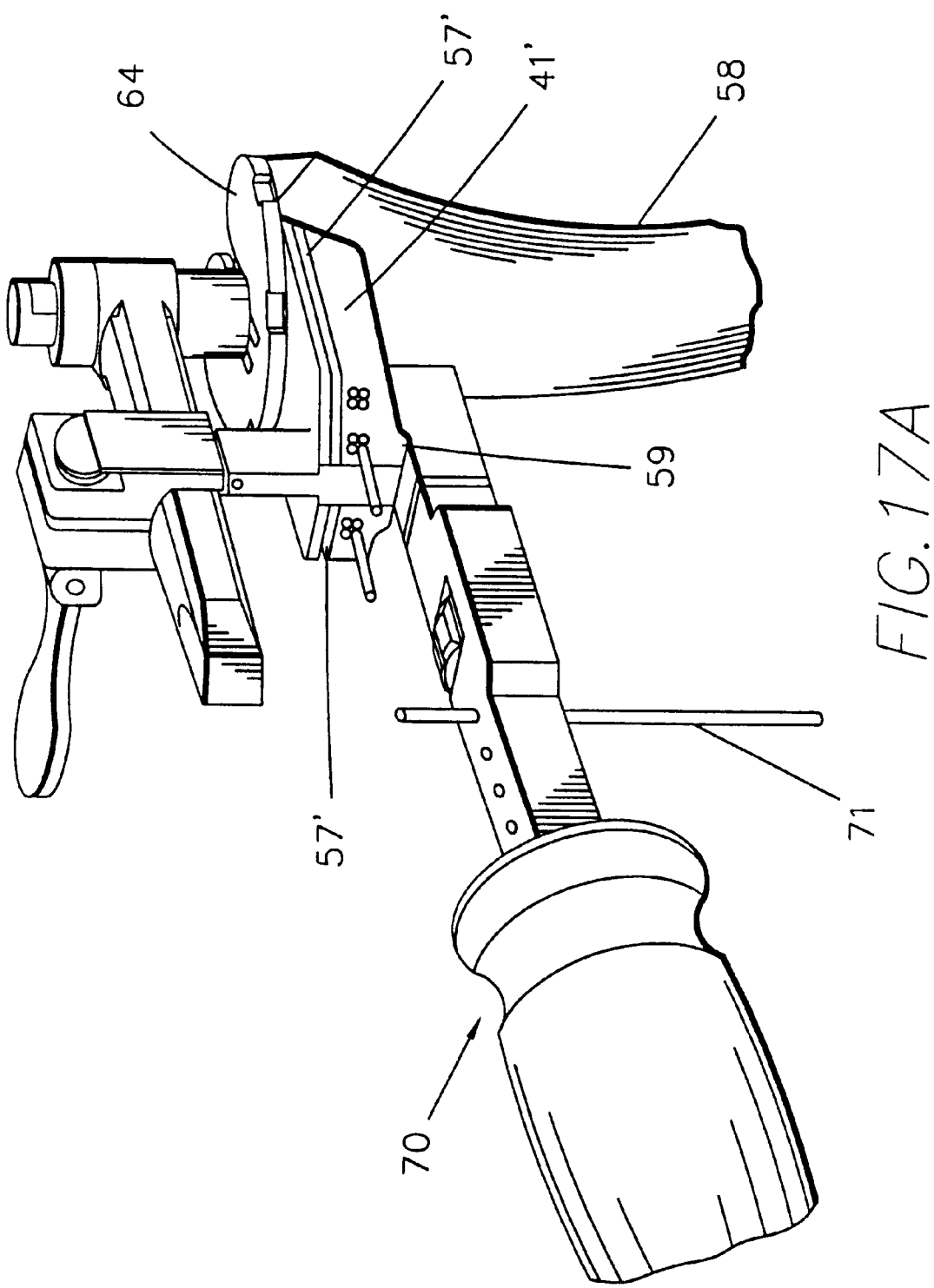
FIG. 17A is a view similar to FIG. 17 of an alternate embodiment of the right tibial cutting block of FIG. 17 with optional EM alignment indicator tools attached.

An alternate embodiment of a tibial cutting block 41Æ is shown in FIG. 17A. The cutting block 41Æ is provided with slots 57Æ for the clean-up cut and a coupling 59 for attaching the handle 70. With the handle 70 and rod 71 attached to the cutting block 41Æ as shown in FIG. 17A, an optional visual EM alignment inspection can be made.

Figure 20:
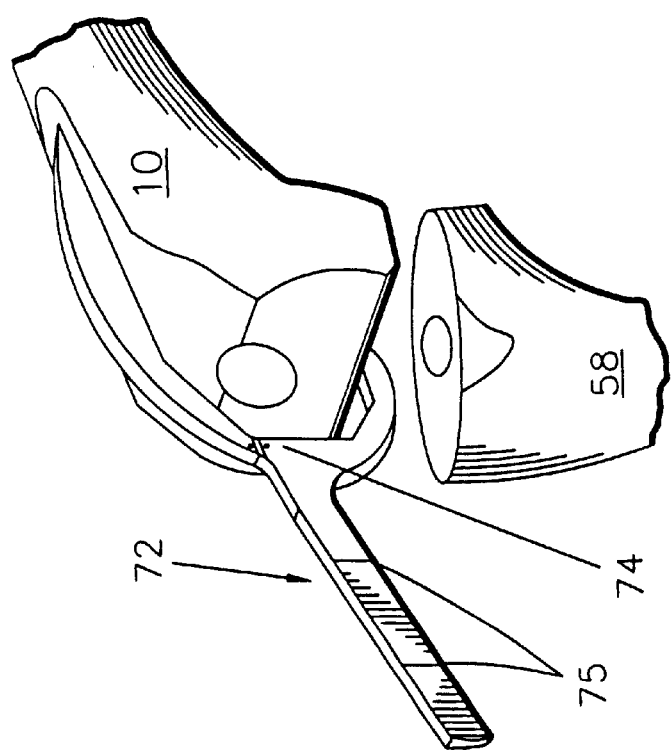
FIG. 20 is a broken perspective view illustrating a tool for sizing of the distal femur and determining the anterior/posterior location of the IM canal.
Figure 19:
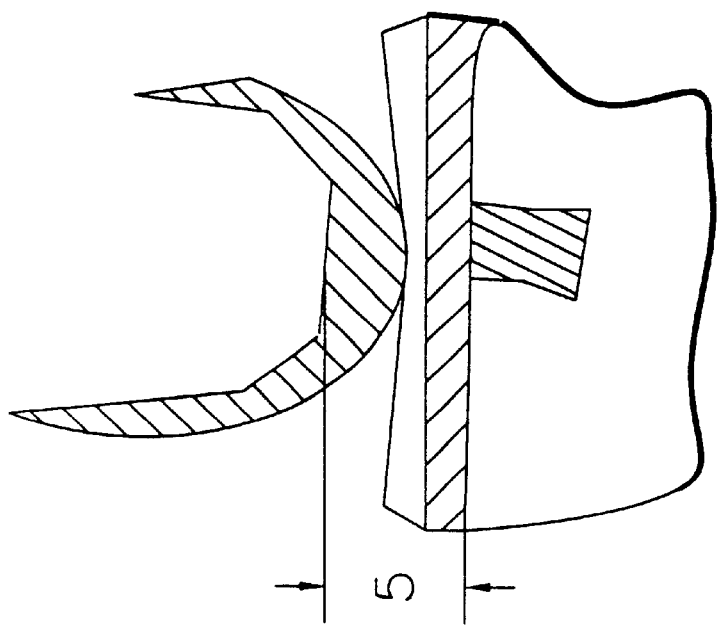
FIG. 19 is a broken schematic view of femoral and tibial components illustrating the thickness of the femoral and tibial components.
Figure 21:
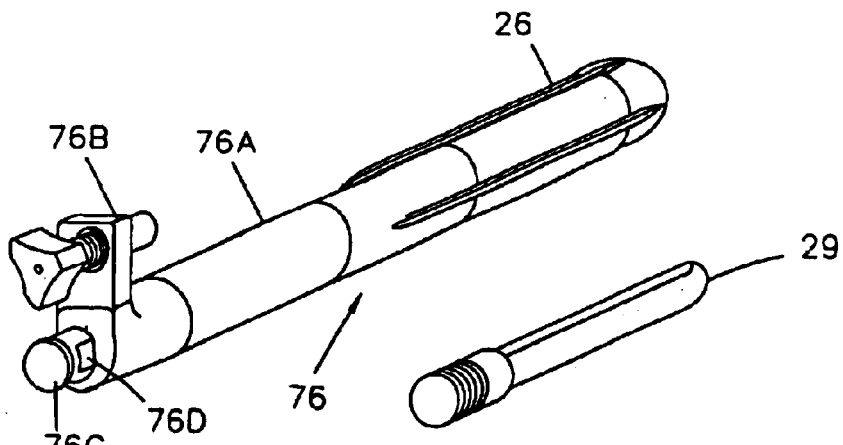
FIG. 21 is a perspective view of the cutting block tool stem assembly and optional IM rod.

Turning now to FIGS. 18–20, after the distal femur and proximal tibia have been resected, the flexion and extension gap is evaluated with a spacer block 68 which is attached to the handle 70. Spacer blocks 68 of different thickness are provided and the thickness corresponds to the combined size "S" in FIG. 19 of both the tibial and femoral components which will be installed.

In the case of wedge cuts, 5 mm and 10 mm wedges 69 are attached to the spacer block 68. The femur 10 is sized using a sizing tool 72 which is provided with markings 74 and 75. The markings 74 are used to measure the amount of anterior/posterior offset of the IM canal. The markings 75 may be used to measure the width of the distal femur by rotating the tool 90 from the position shown. Several different sized tools 72 are provided which correspond in size to the femoral component which will be installed. The shape of the tool 72 corresponds to the silhouette of the femoral component in the saggital plane.

After the tibia and femur have been measured, and a suitable implant chosen for each, the distal femur is prepared to receive the femoral component.

Turning now to FIGS. 21–24, an all-in-one cutting guide 80 is installed with a trial stem valgus adapter 76 which is attached to either a trial stem 26 or an IM rod 29. The trial stem adapter 76 has a threaded boss 76a which is similar to the boss of the tower 28 described above. In addition, the adapter 76 has a spring-loaded bolt 76b and a proximal coupling 76c with grooves 76d. According to one embodiment, the valgus adapter 76 is provided in two sizes: neutral and 4 mm offset and different adapters are provided for left and right knee.

According to a presently preferred embodiment, the all-in-one cutting guide 80 is provided in eight sizes, each corresponding to one of the eight different sized femoral components. The same cutting guide 80 is used for both left and right knees.

Figure 23:
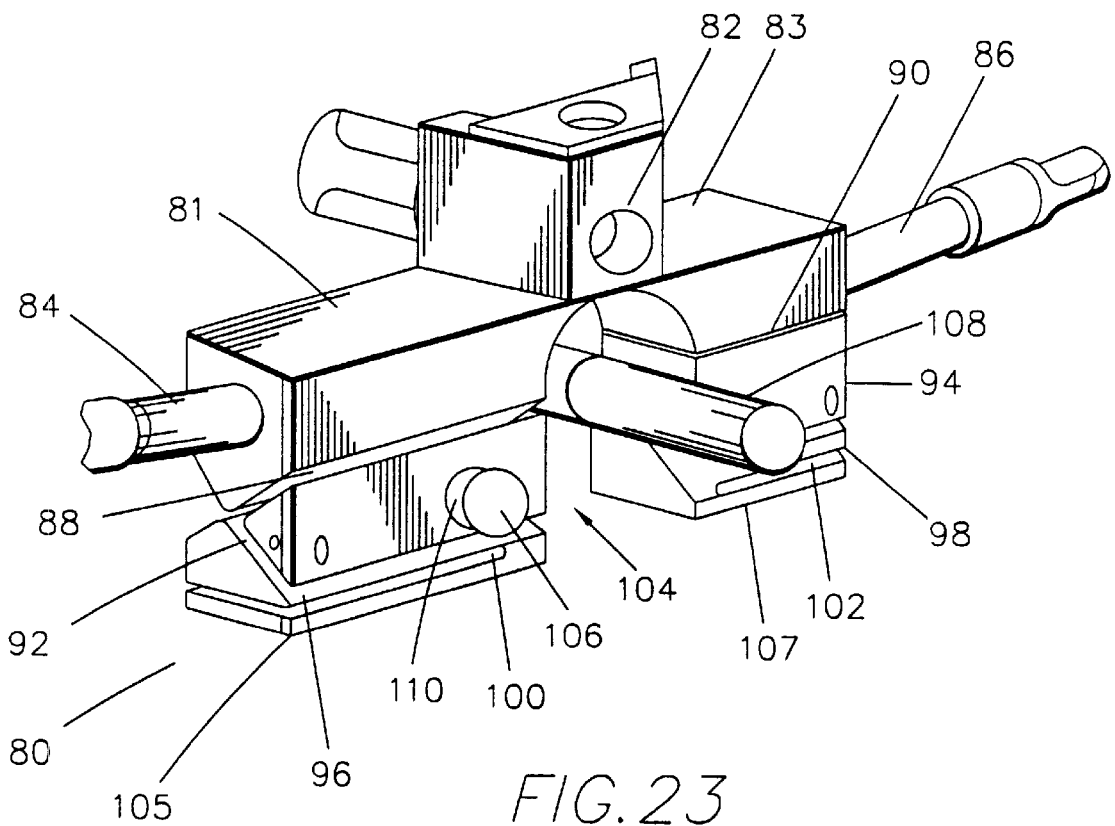
FIG. 23 is a perspective view of the distal side of the all-in-one cutting block with the tool stem attached without the trial stem and with a 5 mm distal spacer attached.

As seen best in FIG. 23, the all-in-one cutting guide 80 is provided with a central anterior threaded coupling 82, medial and lateral handles 84, 86, anterior chamfer cutting guide slots 88, 90, posterior chamfer cutting guide slots 92, 94, and posterior wedge cutting guide slots 96, 98, 100, 102. The anterior surfaces 81, 83 and posterior surfaces 105, 107 may also be used as cutting guides. The threaded coupling 82 receives the bolt 76b of the adapter 76 and a central opening 104 is provided below the threaded coupling 82 for receiving the trial stem 26 and a posterior stabilizer box cutting template (described below).

According to an alternate embodiment, only two valgus adapters 76 are provided (left and right) and the anterior/posterior offset of the cutting guide 80 is effected by providing additional threaded couplings 82 spaced apart from each other in the saggital plane. According to still another embodiment, the anterior/posterior offset is effected via the valgus adapter having an anterior/posterior movable screw.

Figure 22:
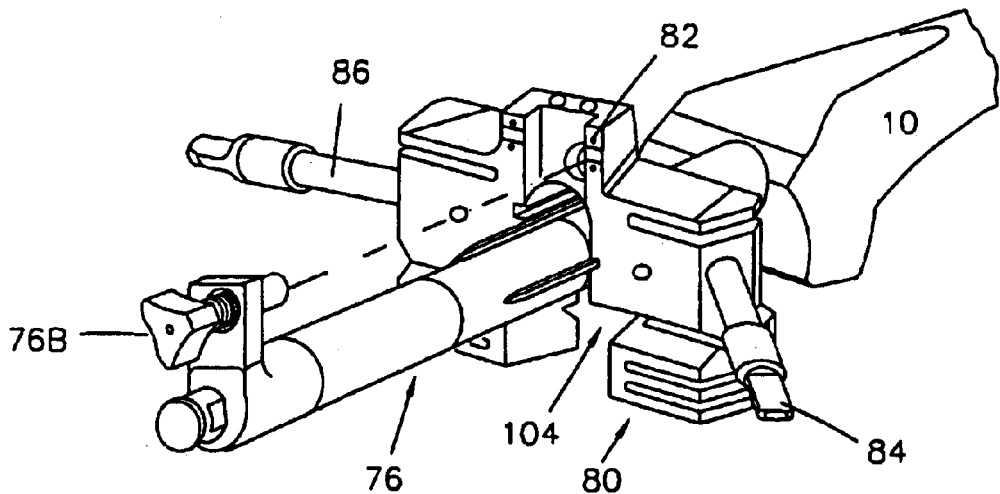
FIG. 22 is a broken and partially exploded perspective view of the all-in-one cutting block, tool stem, and distal femur.
Figure 22A:
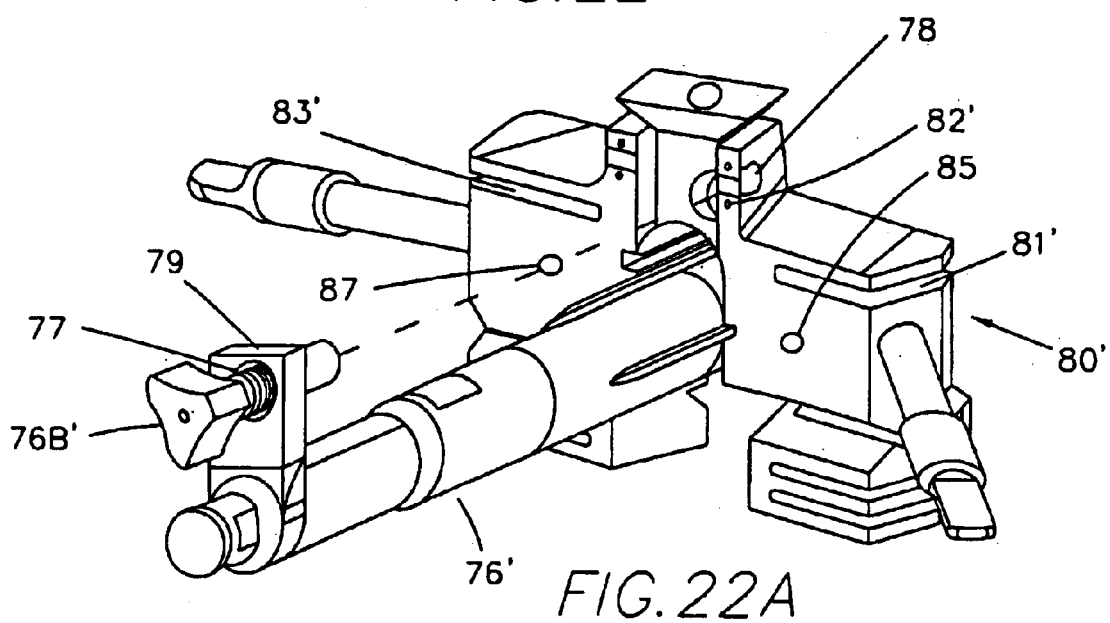
FIG. 22A is a perspective view of an alternate embodiment of the all-in-one cutting block and an alternate embodiment of the valgus adapter.

Alternate embodiments of a cutting block 80' and a valgus adapter 76' are shown in FIG. 22A. The valgus adapter 76' has a bolt 76'b which floats in a slotted tab 77 which is provided with an anterior witness mark 79. Witness marks 78 are provided on the cutting block 80' adjacent to the threaded coupling 82'. It will be appreciated that when the bolt 76'b is attached to the coupling 82', but before it is fully tightened, the valgus adapter 76' may be positioned anteriorally-posteriorally relative to the cutting block 80'. Alignment of the marks 78, 79 will indicate the appropriate position of the valgus adapter. The cutting block 80' also differs from the cutting block 80 in several other respects. In particular, the cutting block 80' has anterior cutting guide slots 81', 83' which some practitioners find preferable to open face guides (81, 83 in FIG. 23). In addition, FIG. 22A shows a pair of alignment holes 85, 87 (which also may be provided in the cutting block 80) which are used in connection with a posterior offset drilling guide which is described below with reference to FIG. 32.

The distal face (the face which faces the distal face of the femur) of the cutting guide 80 is provided with snap fittings 106, 108 for attaching a 5 mm or 10 mm wedge spacer 110 if wedge cuts had been made in the femur. Drill holes 112, 114 are also provided for securing the block to the distal femur as described below.

The trial stem 26 and adapter 76 are attached to the cutting guide 80 as shown in FIGS. 22 and 23 by threading the bolt 76b into the threaded coupling 82. The impactor/extractor tool (30 in FIG. 6) is attached to the coupling 76c, 76d of the adapter and the trial stem is installed in the IM canal of the femur as described above with respect to the tower 28. If the tower 28 had been installed with an 8 mm IM rod 29 rather than the trial stem 26, the IM rod 29 will be used with the valgus adapter 76. After the valgus adapter 76 is installed in the IM canal with the cutting guide 80 attached to it, the impactor/extractor is removed from the valgus adapter.

Rotational alignment of the cutting guide 80 is effected by referencing the posterior condyles of the femur, if they are present, or by aligning the cutting block parallel to the transepicondylar axis with the aid of the handles 84, 86. The spacer block 68 may also be used to aid in rotational alignment as well as to make an assessment of the flexion gap with the cutting guide 80 in place as shown in FIG. 25.

Figure 24:
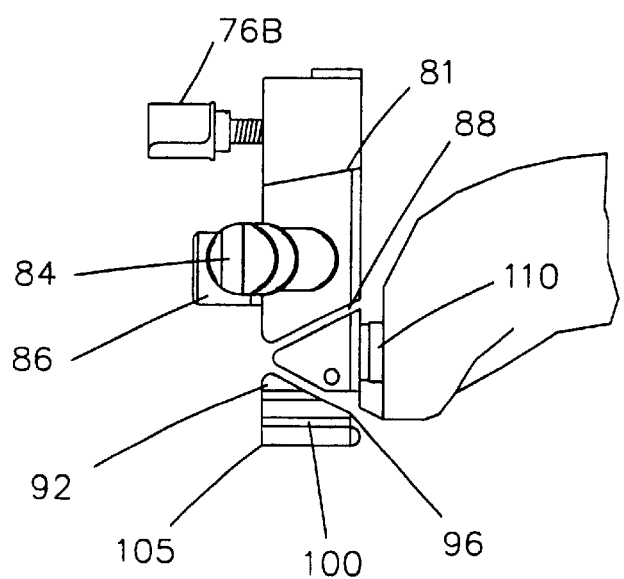
FIG. 24 is a broken side elevational view of the all-in-one cutting block attached to the distal femur.
Figure 25:
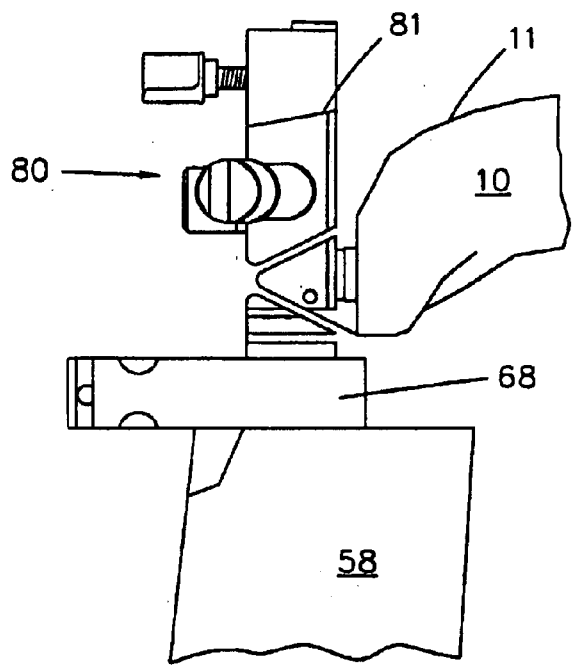
FIG. 25 is a broken side elevational view of the all-in-one cutting block attached to the distal femur with a spacer block resting on the proximal tibia for aiding rotational alignment.
Figure 26:
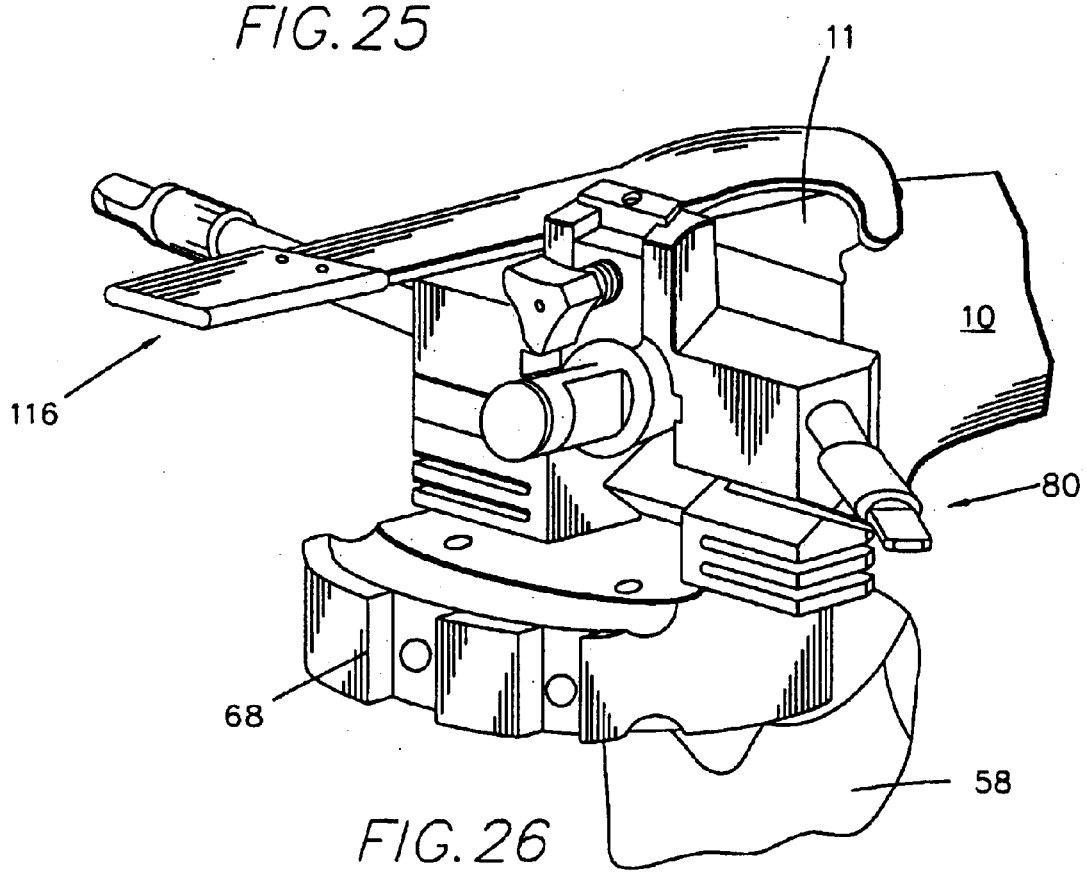
FIG. 26 is a broken perspective view of the all-in-one cutting block attached to the distal femur with a spacer block resting on the proximal tibia and with a sizing indicator attached.

After the cutting guide 80 is installed as shown in FIG. 24 or 25, confirmation of the cutting guide size is made before making any cuts. As shown in FIG. 26, a sizing indicator 116 is placed on the top surface 81 of the cutting guide 80 and references the anterior cortex 11 of the femur 10. The indicator 116 is essentially a hooked blade which indicates whether or not the top surface 81 of the cutting guide 80 and the anterior cortex 11 of the femur 10 lie in substantially the same plane. If it is determined that the cutting guide 80 is the wrong size, the guide 80 and the adapter 76 are removed using the impactor/extractor tool and a new cutting guide 80 is chosen and installed.

After the cutting guide 80 is in the proper position and its size has been confirmed, pins (or drills) are used to stabilize its position.

Figure 27:
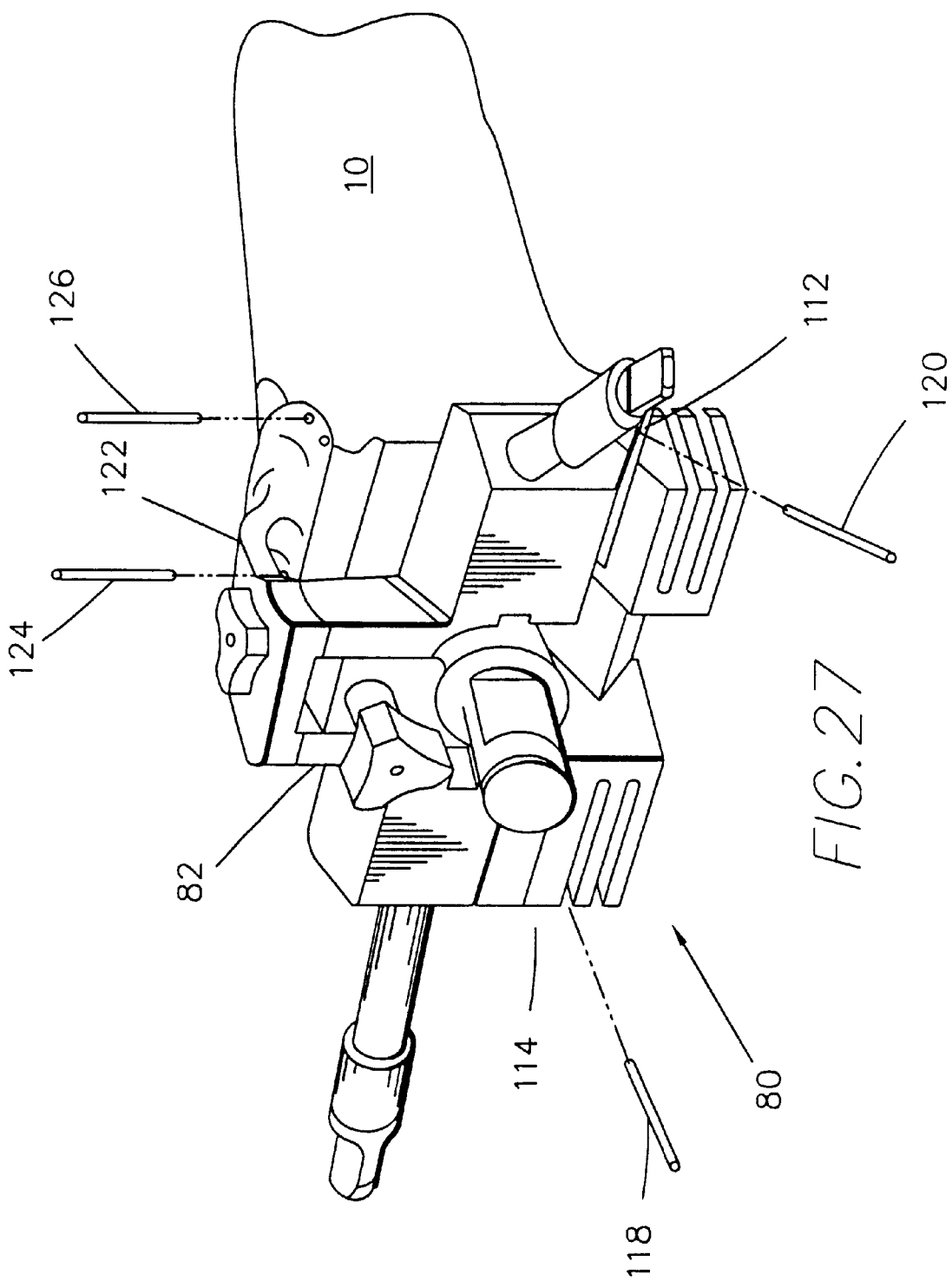
FIG. 27 is a broken perspective view of the all-in-one cutting block attached to the distal femur with the optional anterior referencing plate and showing the location of pins used to secure the cutting block to the femur.

For example, as shown in FIG. 27, ⅛" pins 118, 120 are placed in the pin receiving holes 112, 114 (see also FIG. 23). If additional stability is required, an anterior referencing plate 122 may be attached to an anterior threaded portion of the coupling 82 of the cutting guide 80. The plate 122 is attached after first making an anterior bone cut and is attached to the anterior of the femur with pins (or drills) 124, 126. In addition to providing added stability, the anterior plate 122 also aids in establishing the proper rotational alignment of the cutting guide 80. Furthermore, the anterior plate 122 may be used in lieu of the trial stem and adapter if IM referencing is not desired or not possible.

Figure 28:
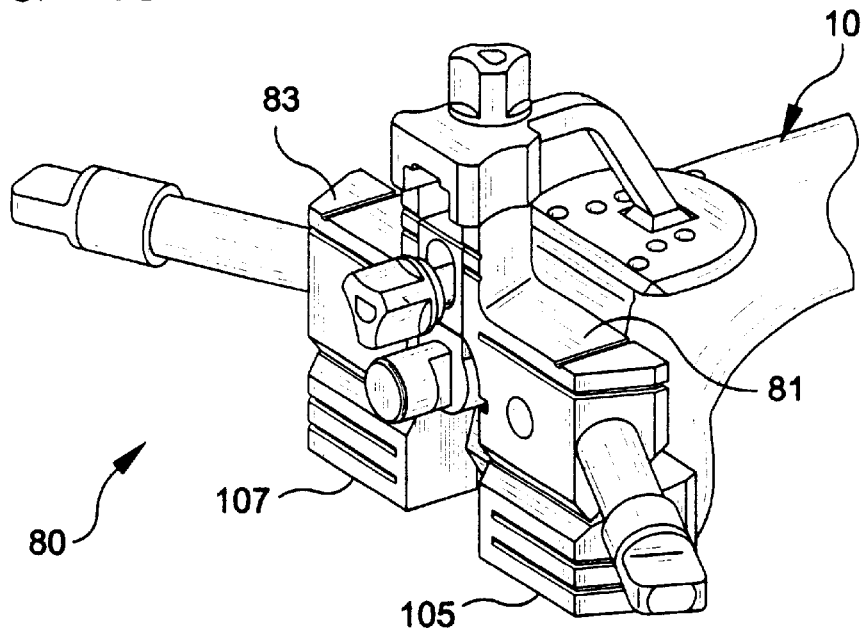
FIG. 28 is a broken perspective view of the all-in-one cutting block attached to the distal femur with the optional anterior referencing plate and in position to make all of the bone cuts in the femur.

With the cutting guide 80 in place as shown in FIG. 28, anterior and posterior resections of the femur are made using the outer surfaces 81, 83, 105, 107 of the guide 80 to guide a cutting blade. Anterior and posterior chamfer cuts are made using the slots 88, 90, 92, 94 which are seen best in FIG. 23. A 5 mm or 10 mm wedge cut may be made using one of the slots 96, 98, 100, 102 which are also seen best in FIG. 23.

Figure 29:
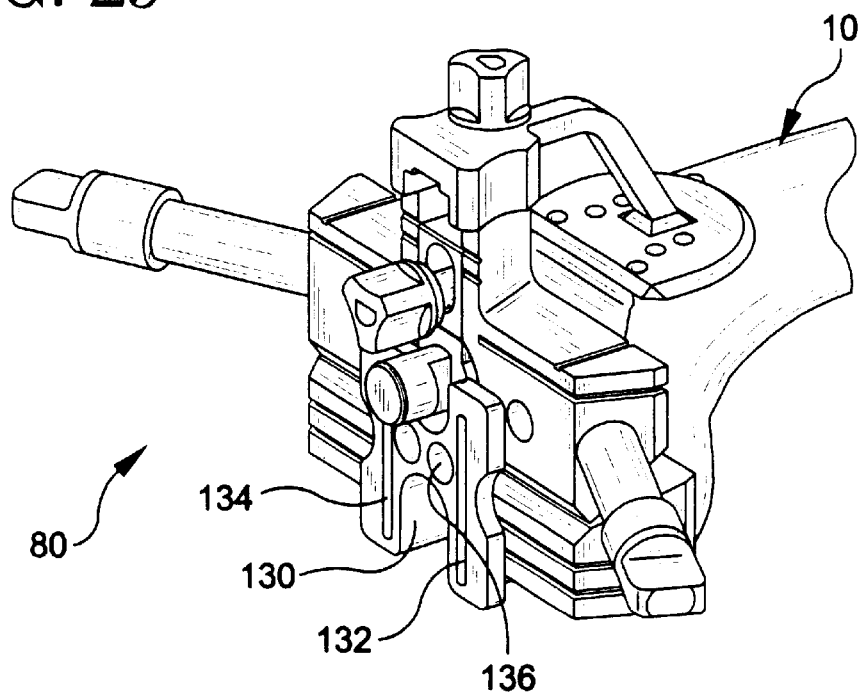
FIG. 29 is a view similar to FIG. 28 with the posterior stabilizer box template attached to the all-in-one cutting block.
Figure 30:
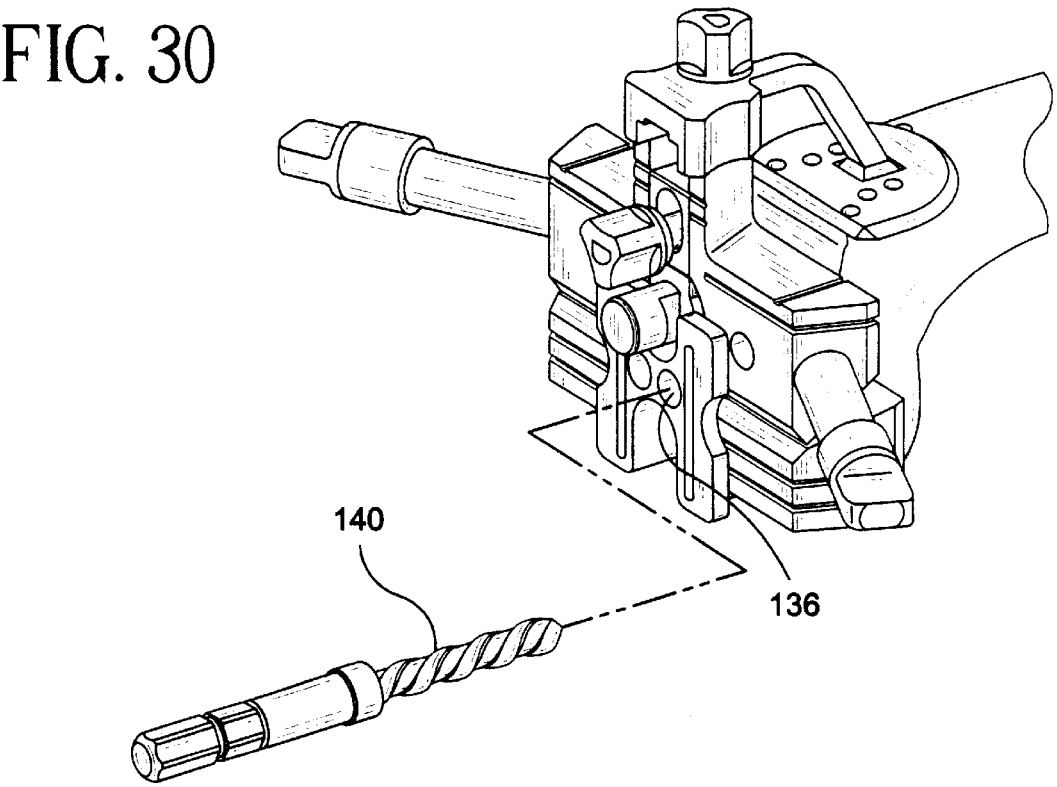
FIG. 30 is a view similar to FIG. 29 illustrating the drill guides in the posterior stabilizer box template.

Turning now to FIG. 29, after the anterior and posterior cuts are made, an appropriately sized stabilizer box guide 130 is attached to the cutting guide 80 if the femoral component will have a posterior stabilizer box. The box guide 130 generally includes a pair of parallel spaced apart chisel guides 132, 134 and a number of drill guides 136. A drill 140 is inserted into the drill guides 136 as shown in FIG. 30. Preferably, two ⁵⁄₁₆" holes are drilled to aid in the removal of bone in the stabilizer box region of the distal femur. The box guide 130 allows the preparation of a stabilizer box cavity while referencing the IM canal.

Figure 31:
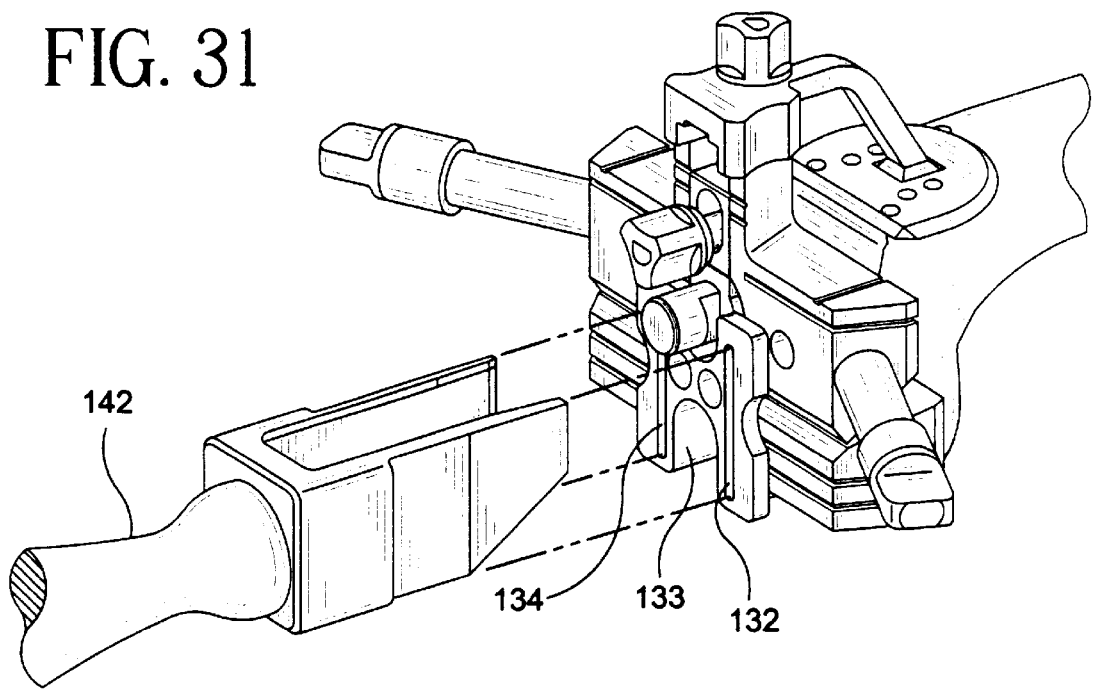
FIG. 31 is a view similar to FIG. 30 illustrating the chisel guides in the posterior stabilizer box template and a chisel.

Prior to inserting a box chisel 142 into the slots 132, 134, as shown in FIG. 31, a ½" osteotome or narrow saw blade is used to cut along the inside wall 133 of the box guide 130. The box chisel 142 is then carefully impacted through the slots 132, 134 and removed.

If the femoral cuts were made with a "neutral" trial stem valgus adapter, the instruments are removed from the femur and the stem 170 shown in FIG. 33 is attached to the boss 164 of the component 160. If, however, the femoral cuts were made with a "4 mm offset" trial stem valgus adapter, a posterior space 19a (FIG. 34) must be made to receive the boss 164 and the 4 mm offset adapter 174 shown in FIG. 34.

Figure 32:
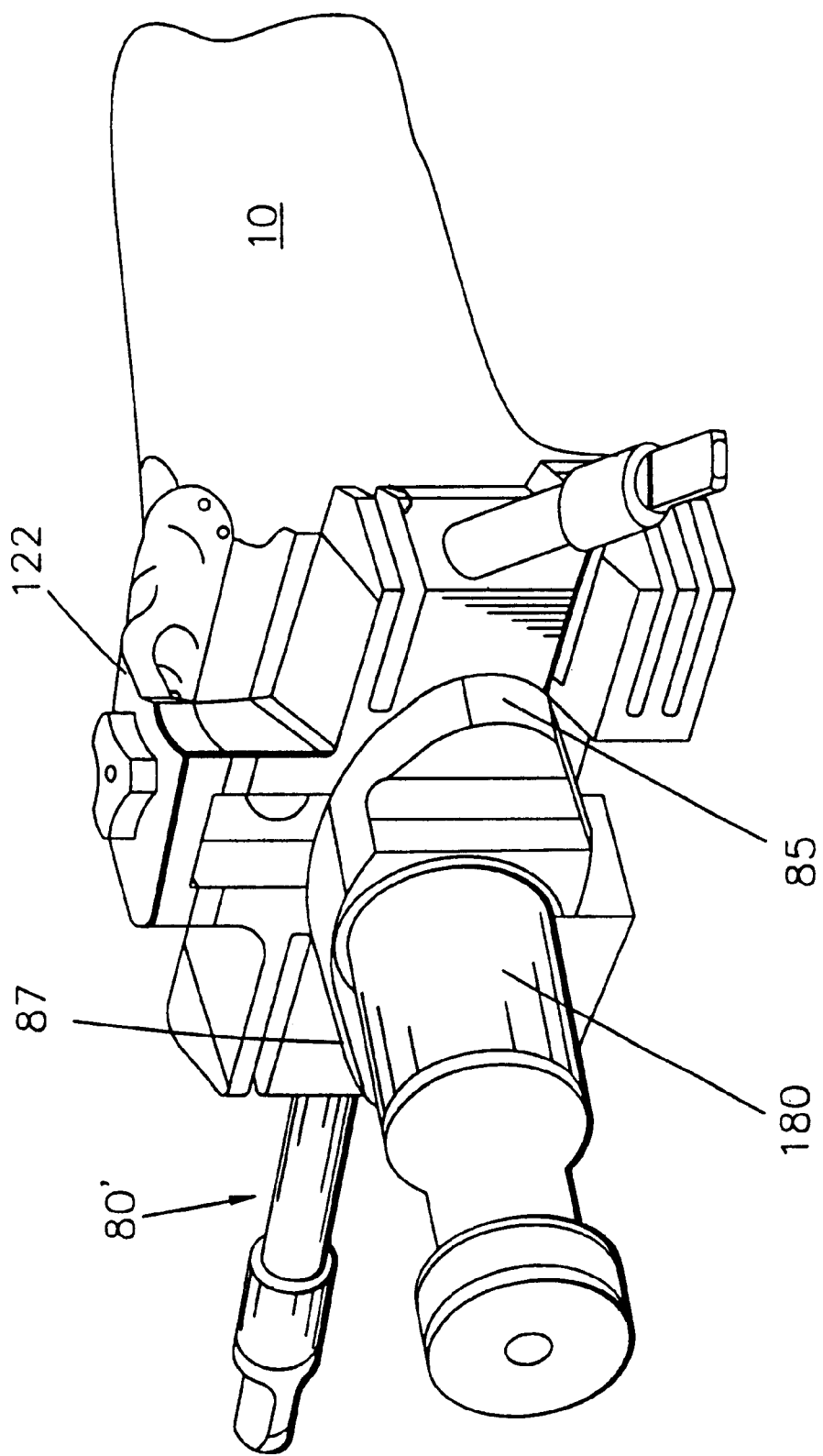
FIG. 32 is broken perspective view of the alternate embodiment all-in-one cutting block with the trial stem and valgus adapter removed and a posterior offset drilling guide attached.

In order to make the posterior space for the boss and the offset adapter, the valgus adapter and trial stem are removed from the cutting block as shown in FIG. 32, and a drilling guide 180 is attached to the cutting guide. The drilling guide 180 attaches to the holes 85, 87 in the cutting block 80' and provides a posterior offset from the IM canal 14 (FIG. 34) so that a cavity 19a can be created between the stabilizer box cavity 19 and the IM canal 14. It will be appreciated that in order to perform this procedure, it is recommended that the anterior referencing plate 122 be attached to the cutting block 80' and the femur 10.

As shown in FIGS. 33 and 34, the femoral component 160 has a bearing surface 162, a threaded boss 164, and a posterior stabilizer box 166. If the femoral cuts were made with a "neutral" trial stem valgus adapter, the stem 170 shown in FIG. 33 is attached to the boss 164 of the component 160. The posterior stabilizer box 166 will be received in the cavity 19 and the stem 170 will be received in the IM canal 14. If, however, the femoral cuts were made with a "4 mm offset" trial stem valgus adapter, the stem 170 is attached to the boss 164 of the component 160 with the aid of a 4 mm offset adapter 174 as shown in FIG. 34. The posteriorly offset boss 164 will be received in the cavity 19a.

Figure 36:
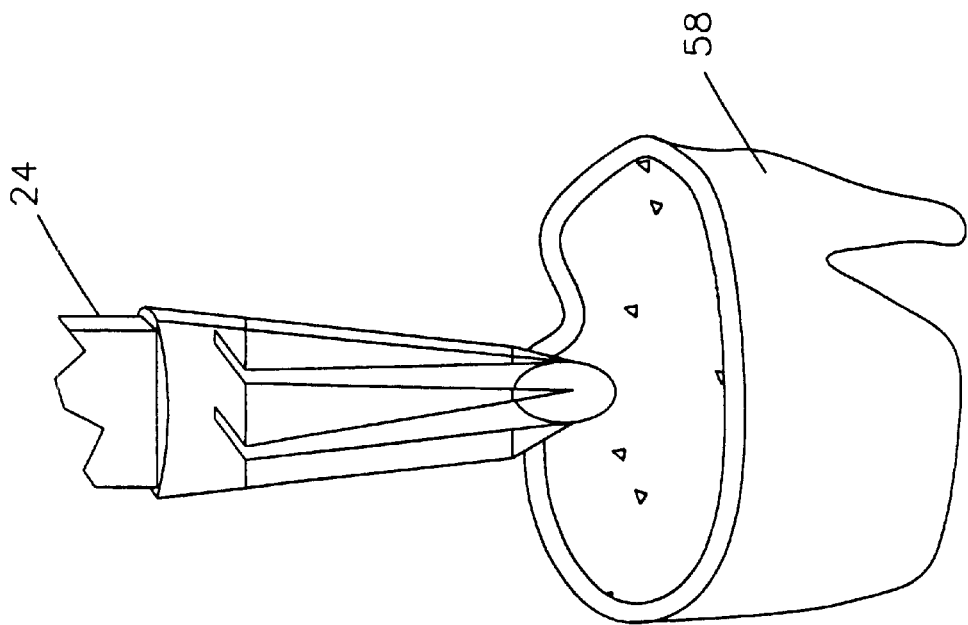
FIG. 36 is a broken perspective view illustrating the second reaming of the tibial IM prior to installation of the tibial component with cement.
Figure 35:
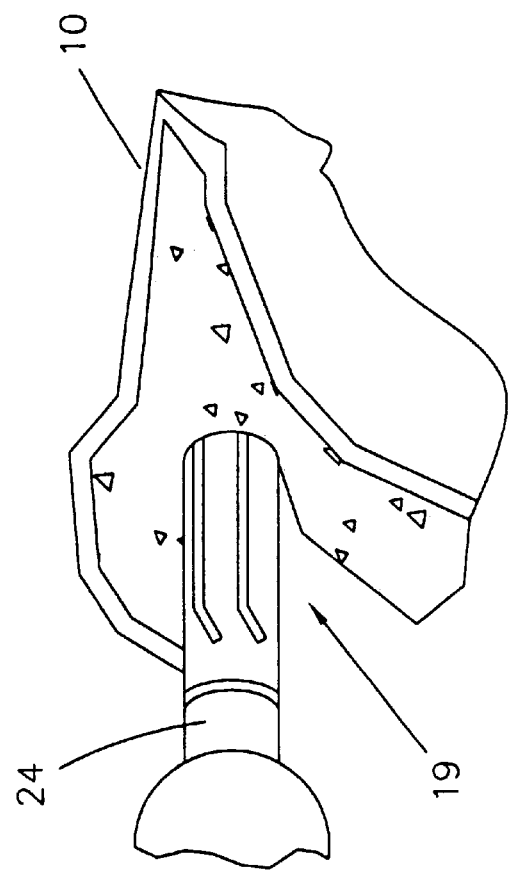
FIG. 35 is a broken perspective view illustrating the second reaming of the femoral IM prior to installation of the femoral component with cement.

Referring now to FIGS. 35 and 36, if the new components will be cemented, reamer 24 is inserted into the IM canals of the femur 10 and tibia 58 and the canals are reamed to accept and properly provide an adequate cement mantle for the stems of the new components. Cement is applied to the interior of the femoral component and to the stem and the component is installed as described above. Similarly, the tibial component is installed in a conventional manner.

There have been described and illustrated herein methods and tools for IM revision surgery. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

What is claimed is:

1. A method of resecting the distal femur and proximal tibia prior to implanting a prosthetic component, said method comprising the steps of:
    (a) securing a block having a plurality of guiding surfaces to the distal femur; and
    (b) resecting the distal femur with said block;
    (c) resecting the anterior cortex of the femur using an anterior cutting guide surface on the block;
    (d) resecting the posterior condyles using a posterior cutting guide surface on the block;
    (e) chamfering the anterior distal femur using an anterior chamfer cutting guide surface on the block;
    (f) chamfering the posterior distal femur using a posterior chamfer cutting guide surface on the block;
    (g) attaching a posterior stabilizer box cutting guide to the block; and
    (h) resecting a posterior stabilizer box cavity.

2. A method according to claim 1 wherein said step of securing further comprises the steps of attaching a valgus adapter to the block and affixing the valgus adapter to the IM canal of the femur.

3. A method according to claim 1 wherein said step of securing further comprises the step of attaching an anterior referencing plate to the block.

4. A method according to claim 1 wherein said step of securing further comprises the step of inserting a pair of pins through holes in the block.

5. A method according to claim 2 wherein said step of attaching a valgus adapter further comprises the step of attaching with a spring biased screw.

6. A method according to claim 1 further comprising the step of rotationally aligning the block with medial and lateral handles prior to resecting the femur.

7. A method according to claim 1 further comprising the step of reaming the femoral IM canal prior to securing the block.

8. A method according to claim 1 further comprising the step of making a clean up cut resection of the distal femur prior to securing the block.

9. The method as set forth in claim 1 further including the step of cutting a cavity for an offset adapter by attaching a cutting guide for the offset adapter to the block.

10. A method of resecting the distal femur and proximal tibia prior to implanting a prosthetic component, said method comprising the steps of:
    (a) placing a guide in the medullary canal;
    (b) measuring the space between the distal femur and the proximal tibia;
    (c) measuring the size of the distal femur;
    (d) mounting a cutting block on said distal femur using said guide as a reference;
    (e) resecting the anterior cortex of the femur using an anterior cutting guide surface on the block;
    (f) resecting the posterior condyles using a posterior cutting guide surface on the block;
    (g) chamfering the anterior distal femur using an anterior chamfer cutting guide surface on the block;
    (h) chamfering the posterior distal femur using a posterior chamfer cutting guide surface on the block;
    (i) attaching a posterior stabilizer box cutting guide to the block; and
    (j) resecting a posterior stabilizer box cavity.

11. The method according to claim 10 further comprising the steps of attaching a valgus adapter to the block and affixing the valgus adapter to the IM canal of the femur.

12. A method according to claim 10 further comprising the step of attaching an anterior referencing plate to the block.

13. A method according to claim 10 further comprising the step of inserting a pair of pins through holes in the block.

14. A method according to claim 11 wherein said step of attaching a valgus adapter further comprises the step of attaching with a spring biased screw.

15. A method according to claim 10 further comprising the step of rotationally aligning the block with medial and lateral handles prior to resecting the femur.

16. A method according to claim 10 further comprising the step of reaming the femoral IM canal prior to securing the block.

17. A method according to claim 10 further comprising the step of making a clean up cut resection of the distal femur prior to securing the block.

18. The method as set forth in claim 10 further including the step of cutting a cavity for an offset adapter by attaching a cutting guide to the block.

19. A method of resecting the distal femur and proximal tibia prior to implanting a prosthetic component, said method comprising the steps of:
    (a) securing a block having a plurality of guiding surfaces to the distal femur;
    (b) resecting the distal femur with said block;
    (c) resecting the anterior cortex of the femur using an anterior cutting guide surface on the block;
    (d) resecting the posterior condyles using a posterior cutting guide surface on the block;
    (e) chamfering the anterior distal femur using an anterior chamfer cutting guide surface on the block;
    (f) chamfering the posterior distal femur using a posterior chamfer cutting guide surface on the block; and
    (g) cutting a cavity for an offset adapter by attaching an offset adapter cutting guide to the block and using said offset cutting guide to form a cavity for the offset adapter.

20. The method as set forth in claim 19 further including the steps of:
    (h) attached a posterior stabilizer box cutting guide to the block; and
    (i) resecting a posterior stabilizer box cavity.

* * * * *